(12) United States Patent
Sampson et al.

(10) Patent No.: US 10,667,914 B2
(45) Date of Patent: Jun. 2, 2020

(54) MYOCARDIAL IMPLANT LOAD SHARING DEVICE AND METHODS TO PROMOTE LV FUNCTION

(71) Applicant: Ancora Heart, Inc., Santa Clara, CA (US)

(72) Inventors: Russel Sampson, Palo Alto, CA (US); Jennifer Henderson, Sunnyvale, CA (US); Jeff Closs, Menlo Park, CA (US); Joshua Sampson, Palo Alto, CA (US); Charles J. Adam, San Jose, CA (US)

(73) Assignee: Ancora Heart, Inc., Santa Clara, CA (US)

(*) Notice: Subject to any disclaimer, the term of this patent is extended or adjusted under 35 U.S.C. 154(b) by 231 days.

(21) Appl. No.: 15/817,015

(22) Filed: Nov. 17, 2017

(65) Prior Publication Data

US 2018/0140421 A1 May 24, 2018

Related U.S. Application Data

(60) Provisional application No. 62/424,120, filed on Nov. 18, 2016.

(51) Int. Cl.
*A61F 2/24* (2006.01)
*A61B 17/04* (2006.01)
(Continued)

(52) U.S. Cl.
CPC ........ *A61F 2/2487* (2013.01); *A61B 17/0401* (2013.01); *A61B 17/0487* (2013.01);
(Continued)

(58) Field of Classification Search
CPC ........ A61F 2/24; A61F 2/2409; A61F 2/2442; A61F 2/2478; A61F 2/2481;
(Continued)

(56) References Cited

U.S. PATENT DOCUMENTS

| 3,656,185 A | 4/1972 | Carpentier |
| 3,727,614 A | 4/1973 | Kniazuk |

(Continued)

FOREIGN PATENT DOCUMENTS

| EP | 0 669 101 A1 | 8/1995 |
| JP | 6-510460 A | 11/1994 |

(Continued)

OTHER PUBLICATIONS

Corbion Purac (2015). Technology Summary, 1 total page.
(Continued)

*Primary Examiner* — Todd J Scherbel
(74) *Attorney, Agent, or Firm* — Cooley LLP

(57) ABSTRACT

The devices and methods described herein may be used to restore left ventricular function to address mitral valve regurgitation. One variation of an implant comprises a plurality of tethered anchors and a plurality of force-distribution members slidably disposed on the tether between the anchors. One or more of the force-distribution members can comprise a bioabsorbable material. Methods comprise deploying the implant to cardiac tissue, cinching the implant to its hard stop (e.g., where further cinching does not cause further tissue tightening), providing a pre-selected amount of slack to the implant after it has been cinched to its hard stop configuration, and securing a lock member on the tether. Also disclosed herein are lock member deployment catheters that provide a pre-selected amount of tether slack as it secures a lock member on the tether.

17 Claims, 32 Drawing Sheets

Short axis view of reduced LV

(51) Int. Cl.
*A61B 17/06* (2006.01)
*A61B 17/00* (2006.01)

(52) U.S. Cl.
CPC ...... *A61B 17/06166* (2013.01); *A61F 2/2436* (2013.01); *A61B 2017/00004* (2013.01); *A61B 2017/00243* (2013.01); *A61B 2017/00783* (2013.01); *A61B 2017/00867* (2013.01); *A61B 2017/00893* (2013.01); *A61B 2017/0409* (2013.01); *A61B 2017/0414* (2013.01); *A61B 2017/0437* (2013.01); *A61B 2017/0448* (2013.01); *A61B 2017/0464* (2013.01); *A61B 2017/0496* (2013.01); *A61B 2017/06176* (2013.01); *A61F 2/2445* (2013.01); *A61F 2/2466* (2013.01); *A61F 2210/0004* (2013.01); *A61F 2210/0014* (2013.01); *A61F 2220/0016* (2013.01)

(58) Field of Classification Search
CPC .... A61F 2/2487; A61F 2/249; A61B 17/0401; A61B 2017/0496
See application file for complete search history.

(56) References Cited

U.S. PATENT DOCUMENTS

| | | | |
|---|---|---|---|
| 3,773,034 A | 11/1973 | Burns et al. | |
| 3,961,419 A | 6/1976 | Schwartz | |
| 3,976,079 A | 8/1976 | Samuels et al. | |
| 4,014,492 A | 3/1977 | Rothfuss | |
| 4,034,473 A | 7/1977 | May | |
| 4,042,979 A | 8/1977 | Angell | |
| 4,043,504 A | 8/1977 | Hueil et al. | |
| 4,053,979 A | 10/1977 | Tuthill et al. | |
| 4,055,861 A | 11/1977 | Carpentier et al. | |
| 4,069,825 A | 1/1978 | Akiyama | |
| 4,290,151 A | 9/1981 | Massana | |
| 4,384,406 A | 5/1983 | Tischlinger | |
| 4,445,892 A | 5/1984 | Hussein et al. | |
| 4,489,446 A | 12/1984 | Reed | |
| 4,494,542 A | 1/1985 | Lee | |
| 4,619,247 A | 10/1986 | Inoue et al. | |
| 4,700,250 A | 10/1987 | Kuriyama | |
| 4,726,371 A | 2/1988 | Gibbens | |
| 4,758,221 A | 7/1988 | Jureidini | |
| 4,784,133 A | 11/1988 | Mackin | |
| 4,845,851 A | 7/1989 | Warthen | |
| 4,848,341 A | 7/1989 | Ahmad | |
| 4,850,354 A | 7/1989 | McGurk-Burleson et al. | |
| 4,961,738 A | 10/1990 | Mackin | |
| 4,969,893 A | 11/1990 | Swor | |
| 4,976,710 A | 12/1990 | Mackin | |
| 5,053,047 A | 10/1991 | Yoon | |
| 5,064,431 A | 11/1991 | Gilbertson et al. | |
| 5,078,731 A | 1/1992 | Hayhurst | |
| 5,084,058 A | 1/1992 | Li | |
| 5,103,804 A | 4/1992 | Abele et al. | |
| 5,133,723 A | 7/1992 | Li et al. | |
| 5,221,255 A | 6/1993 | Mahurkar et al. | |
| 5,221,269 A | 6/1993 | Miller et al. | |
| 5,242,456 A | 9/1993 | Nash et al. | |
| 5,257,975 A | 11/1993 | Foshee | |
| 5,312,341 A | 5/1994 | Turi | |
| 5,324,298 A | 6/1994 | Phillips et al. | |
| 5,346,500 A | 9/1994 | Suchart | |
| 5,358,479 A | 10/1994 | Wilson | |
| 5,364,407 A | 11/1994 | Poll | |
| 5,366,479 A | 11/1994 | McGarry et al. | |
| 5,368,591 A | 11/1994 | Lennox et al. | |
| 5,383,905 A | 1/1995 | Golds et al. | |
| 5,409,483 A | 4/1995 | Campbell et al. | |
| 5,409,499 A | 4/1995 | Yi | |
| 5,417,700 A | 5/1995 | Egan | |
| 5,423,837 A | 6/1995 | Mericle et al. | |
| 5,437,680 A | 8/1995 | Yoon | |
| 5,439,470 A | 8/1995 | Li | |
| 5,450,860 A | 9/1995 | O'Connor | |
| 5,452,513 A | 9/1995 | Zinnbauer et al. | |
| 5,474,572 A | 12/1995 | Hayhurst | |
| 5,520,702 A | 5/1996 | Sauer et al. | |
| 5,522,873 A | 6/1996 | Jackman et al. | |
| 5,524,630 A | 6/1996 | Crowley | |
| 5,527,323 A | 6/1996 | Jervis et al. | |
| 5,545,134 A | 8/1996 | Hilaire et al. | |
| 5,545,168 A | 8/1996 | Burke | |
| 5,565,122 A | 10/1996 | Zinnbauer et al. | |
| 5,571,215 A | 11/1996 | Sterman et al. | |
| 5,591,194 A | 1/1997 | Berthiaume | |
| 5,626,614 A | 5/1997 | Hart | |
| 5,630,824 A | 5/1997 | Hart | |
| 5,643,289 A | 7/1997 | Sauer et al. | |
| 5,669,917 A | 9/1997 | Sauer et al. | |
| 5,674,279 A | 10/1997 | Wright et al. | |
| 5,690,655 A | 11/1997 | Hart et al. | |
| 5,709,695 A | 1/1998 | Northrup, III | |
| 5,713,950 A | 2/1998 | Cox | |
| 5,716,370 A | 2/1998 | Williamson, IV et al. | |
| 5,718,725 A | 2/1998 | Sterman et al. | |
| 5,722,403 A | 3/1998 | McGee et al. | |
| 5,725,542 A | 3/1998 | Yoon | |
| 5,735,290 A | 4/1998 | Sterman et al. | |
| 5,741,260 A | 4/1998 | Songer et al. | |
| 5,741,301 A | 4/1998 | Pagedas | |
| 5,752,518 A | 5/1998 | McGee et al. | |
| 5,752,964 A | 5/1998 | Mericle | |
| 5,752,966 A | 5/1998 | Chang | |
| 5,755,730 A | 5/1998 | Swain et al. | |
| 5,766,240 A | 6/1998 | Johnson | |
| 5,769,812 A | 6/1998 | Stevens et al. | |
| 5,782,861 A | 7/1998 | Cragg et al. | |
| 5,810,848 A | 9/1998 | Hayhurst | |
| 5,810,853 A | 9/1998 | Yoon | |
| 5,817,107 A | 10/1998 | Schaller | |
| 5,827,171 A | 10/1998 | Dobak, III et al. | |
| 5,843,169 A | 12/1998 | Taheri | |
| 5,848,969 A | 12/1998 | Panescu et al. | |
| 5,860,992 A | 1/1999 | Daniel et al. | |
| 5,860,993 A | 1/1999 | Thompson et al. | |
| 5,868,733 A | 2/1999 | Ockuly et al. | |
| 5,879,371 A | 3/1999 | Gardiner et al. | |
| 5,885,238 A | 3/1999 | Stevens et al. | |
| 5,888,240 A | 3/1999 | Carpentier et al. | |
| 5,902,321 A | 5/1999 | Caspari et al. | |
| 5,904,651 A | 5/1999 | Swanson et al. | |
| 5,906,579 A | 5/1999 | Vander Salm et al. | |
| 5,919,208 A | 7/1999 | Valenti | |
| 5,935,149 A | 8/1999 | Ek | |
| 5,947,983 A | 9/1999 | Solar et al. | |
| 5,961,440 A | 10/1999 | Schweich, Jr. et al. | |
| 5,961,539 A | 10/1999 | Northrup, III et al. | |
| 5,972,004 A | 10/1999 | Williamson, IV et al. | |
| 5,989,284 A | 11/1999 | Laufer | |
| 5,991,650 A | 11/1999 | Swanson et al. | |
| 6,010,531 A | 1/2000 | Donlon et al. | |
| 6,015,428 A | 1/2000 | Pagedas | |
| 6,042,534 A | 3/2000 | Gellman et al. | |
| 6,050,936 A | 4/2000 | Schweich, Jr. et al. | |
| 6,059,715 A | 5/2000 | Schweich, Jr. et al. | |
| 6,066,160 A | 5/2000 | Colvin et al. | |
| 6,074,401 A | 6/2000 | Gardiner et al. | |
| 6,077,214 A | 6/2000 | Mortier et al. | |
| 6,077,989 A | 6/2000 | Kandel et al. | |
| 6,099,553 A | 8/2000 | Hart et al. | |
| 6,125,852 A | 10/2000 | Stevens et al. | |
| 6,149,658 A | 11/2000 | Gardiner et al. | |
| 6,162,168 A | 12/2000 | Schweich, Jr. et al. | |
| 6,165,183 A | 12/2000 | Kuehn et al. | |
| 6,171,329 B1 | 1/2001 | Shaw et al. | |
| 6,183,469 B1 | 2/2001 | Thapliyal et al. | |
| 6,197,017 B1 | 3/2001 | Brock et al. | |
| 6,210,432 B1 | 4/2001 | Solem et al. | |
| 6,221,084 B1 | 4/2001 | Fleenor | |
| 6,228,096 B1 | 5/2001 | Marchand | |

(56) References Cited

U.S. PATENT DOCUMENTS

| | | |
|---|---|---|
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,326,231 B2 | 2/2008 | Phillips et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,727,247 B2 | 6/2010 | Kimura et al. |
| 7,753,858 B2 | 7/2010 | Starksen et al. |
| 7,753,922 B2 | 7/2010 | Starksen |
| 7,753,924 B2 | 7/2010 | Starksen et al. |
| 7,758,637 B2 | 7/2010 | Starksen et al. |
| 7,766,812 B2 | 8/2010 | Schroeder et al. |
| 7,850,600 B1 | 12/2010 | Piskun |
| 7,922,762 B2 | 4/2011 | Starksen |
| 8,066,766 B2 | 11/2011 | To et al. |
| 8,343,173 B2 | 1/2013 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2002/0013621 A1 | 1/2002 | Stobie et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0171776 A1 | 9/2003 | Adams et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0097788 A1 | 5/2004 | Mourlas et al. |
| 2004/0122450 A1 | 6/2004 | Oren et al. |
| 2004/0172046 A1 | 9/2004 | Hlavka et al. |
| 2004/0181238 A1 | 9/2004 | Zarbatany et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119523 A1 | 6/2005 | Starksen et al. |
| 2005/0119673 A1 | 6/2005 | Gordon et al. |
| 2005/0119734 A1 | 6/2005 | Spence et al. |

(56) References Cited

U.S. PATENT DOCUMENTS

| | | |
|---|---|---|
| 2005/0119735 A1 | 6/2005 | Spence et al. |
| 2005/0125011 A1 | 6/2005 | Spence et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228448 A1 | 10/2005 | Li |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267571 A1 | 12/2005 | Spence et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0080188 A1 | 4/2007 | Spence et al. |
| 2007/0112422 A1 | 5/2007 | Dehdashtian |
| 2007/0112424 A1 | 5/2007 | Spence et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0243150 A1 | 10/2008 | Starksen et al. |
| 2008/0294177 A1 | 11/2008 | To et al. |
| 2009/0182417 A1 | 7/2009 | Tremulis et al. |
| 2009/0276038 A1 | 11/2009 | Tremulis et al. |
| 2010/0023117 A1 | 1/2010 | Yoganathan et al. |
| 2010/0076548 A1 | 3/2010 | Konno |
| 2010/0094314 A1 | 4/2010 | Hernlund et al. |
| 2011/0098743 A1 | 4/2011 | Lyons et al. |
| 2011/0276091 A1 | 11/2011 | Melanson et al. |
| 2013/0190863 A1 | 7/2013 | Call et al. |
| 2015/0230919 A1* | 8/2015 | Chau ..................... A61F 2/246 623/2.11 |
| 2018/0228609 A1 | 8/2018 | Starksen et al. |

FOREIGN PATENT DOCUMENTS

| | | |
|---|---|---|
| JP | 11-506628 A | 6/1999 |
| WO | WO 93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO 96/39081 A1 | 12/1996 |
| WO | WO-96/39942 A1 | 12/1996 |
| WO | WO-97/27799 A1 | 8/1997 |
| WO | WO-97/27807 A1 | 8/1997 |
| WO | WO 97/30639 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/00099 A2 | 1/2002 |
| WO | WO-02/00099 A3 | 1/2002 |
| WO | WO-02/03892 A1 | 1/2002 |
| WO | WO-02/051329 A1 | 7/2002 |
| WO | WO-02/053011 A2 | 7/2002 |
| WO | WO-02/053011 A3 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO 2007/001936 A2 | 1/2007 |
| WO | WO 2007/001936 A3 | 1/2007 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2008/028135 A2 | 3/2008 |
| WO | WO-2008/028135 A3 | 3/2008 |

OTHER PUBLICATIONS

Corbion Purac (2015). PURASORB® Polymers: Products for Medical Devices, 2 total pages.

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.

De Simone, R. et al. (Apr. 1, 1994). "Adjustable Annuloplasty for Tricuspid Insufficiency with External Control," *Reader's Comments and Reply, Am. J. Cardiol.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.

International Search Report and Written Opinion dated Mar. 8, 2018, for PCT Patent Application No. PCT/US2017/062382, filed on Nov. 17, 2017, 15 pages.

Nagy, Z.L. et al. (Dec. 2000). "Mitral Annuloplasty with a Suture Technique," *European Journal of Cardio-thoracic Surgery* 18(6):739-740.

Non-Final Office Action dated Apr. 30, 2009, for U.S. Appl. No. 10/901,444, filed Jul. 27, 2004, 9 pages.

Non-Final Office Action dated Jan. 16, 2008, for U.S. Appl. No. 10/901,444, filed Jul. 27, 2004, 9 pages.

Non-Final Office Action dated Jan. 17, 2007, for U.S. Appl. No. 10/901,444, filed Jul. 27, 2004, 11 pages.

Final Office Action dated Oct. 19, 2009, for U.S. Appl. No. 10/901,444, filed Jul. 27, 2004, 9 pages.

(56) References Cited

OTHER PUBLICATIONS

Final Office Action dated Aug. 19, 2008, for U.S. Appl. No. 10/901,444, filed Jul. 27, 2004, 9 pages.
Final Office Action dated Sep. 11, 2007, for U.S. Appl. No. 10/901,444, filed Jul. 27, 2004, 10 pages.
Notice of Allowance dated Mar. 29, 2010, for U.S. Appl. No. 10/901,444, filed Jul. 27, 2004, 7 pages.
Non-Final Office Action dated Dec. 21, 2010, for U.S. Appl. No. 12/133,306, filed Jun. 4, 2008, 13 pages.
Non-Final Office Action dated Feb. 17, 2012, for U.S. Appl. No. 12/133,319, filed Jun. 4, 2008, 7 pages.
Non-Final Office Action dated Dec. 16, 2010, for U.S. Appl. No. 12/133,319, filed Jun. 4, 2008, 10 pages.
Final Office Action dated Jul. 11, 2011, for U.S. Appl. No. 12/133,319, filed Jun. 4, 2008, 8 pages.
Notice of Allowance dated Aug. 30, 2012, for U.S. Appl. No. 12/133,319, filed Jun. 4, 2008, 8 pages.
Saito, E. et al. (2010). "Experimental and computational characterization of designed and fabricated 50:50 PLGA porous scaffolds for human trabecular bone applications," *J. Mater Sci. Mater Med.* 21:2371-2383.
Shumway, S.J. et al. (Dec. 1988). "A 'Designer' Annuloplasty Ring for Patients with Massive Mitral Annular Dilatation," *Ann. Thorac. Surg.* 46(6):695-696.

\* cited by examiner

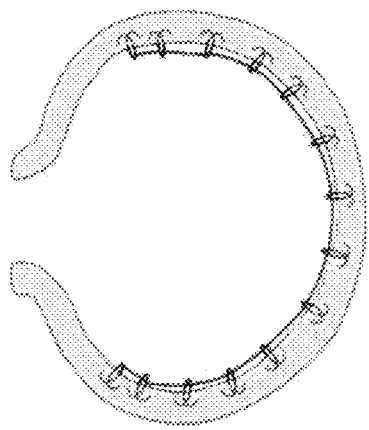
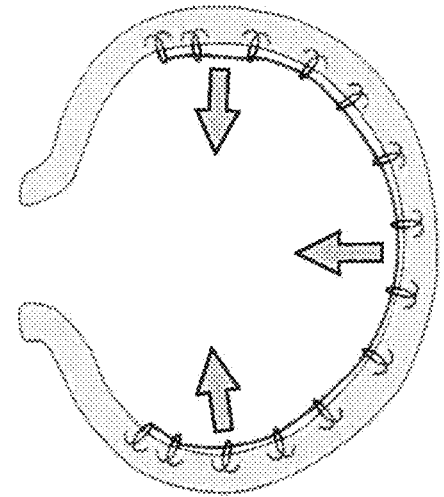
FIG. 1C Short axis view of LV     FIG. 1D Short axis view of reduced LV
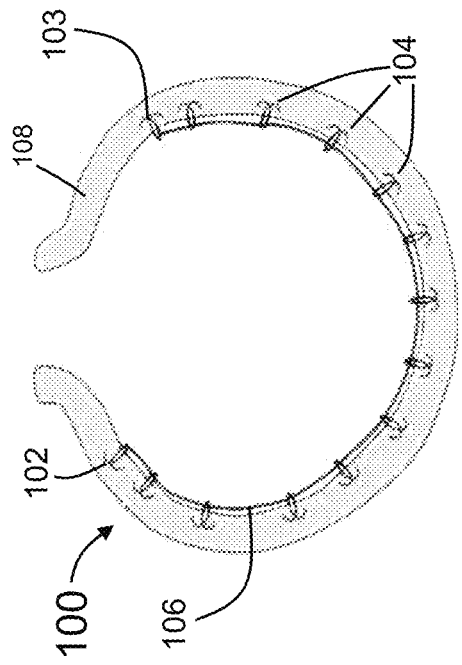
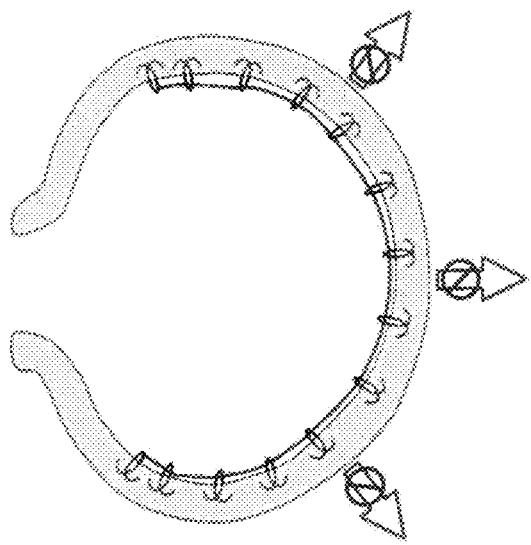
FIG. 1E Implant prevents distension     FIG. 1F Implant allows contraction

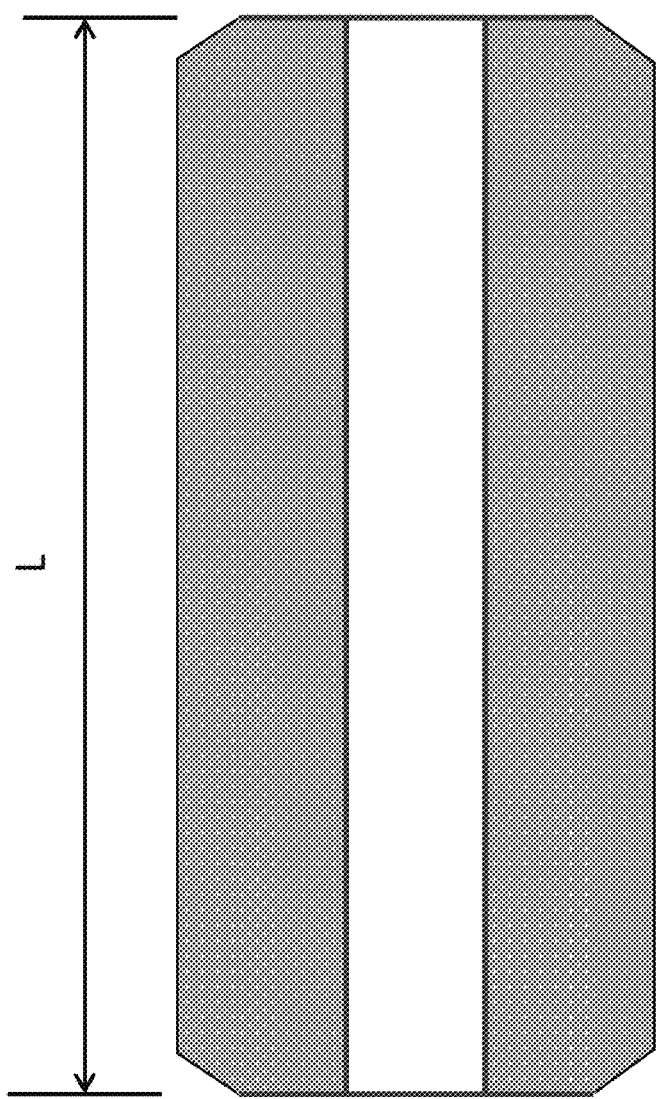
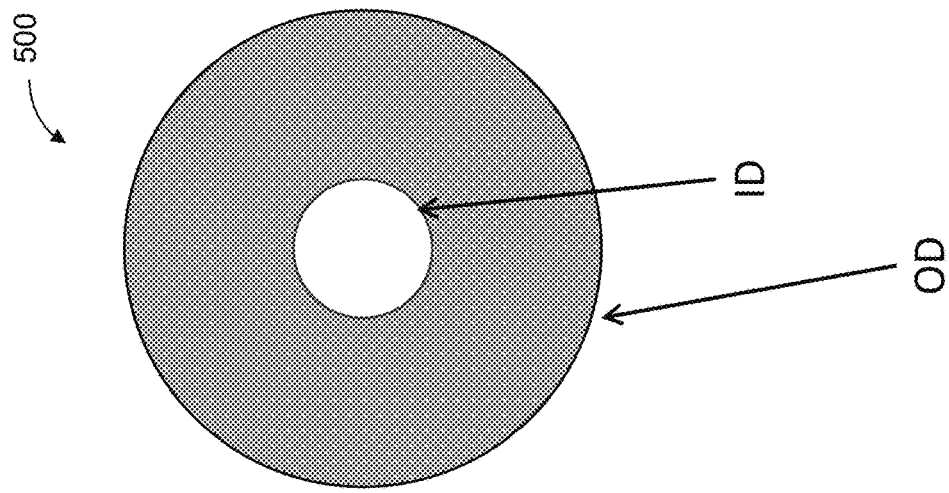
FIG. 5A
FIG. 5B

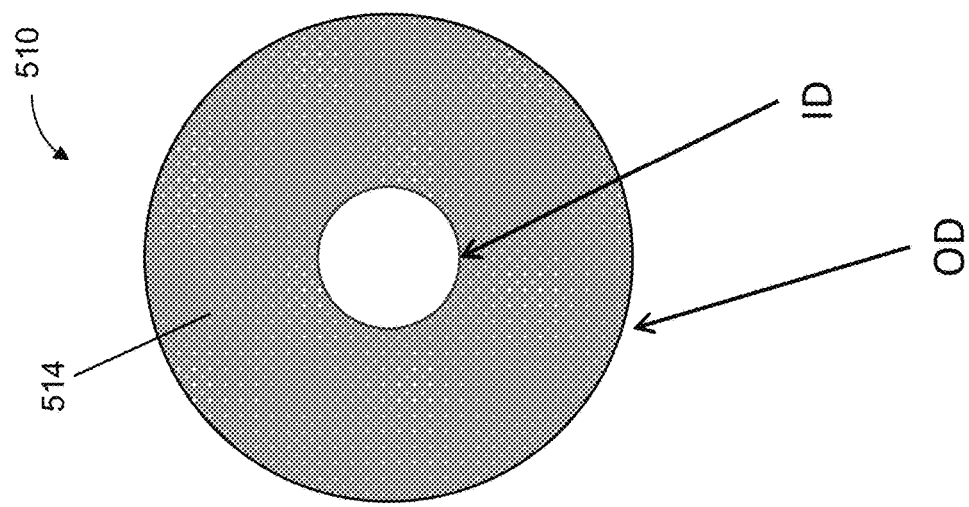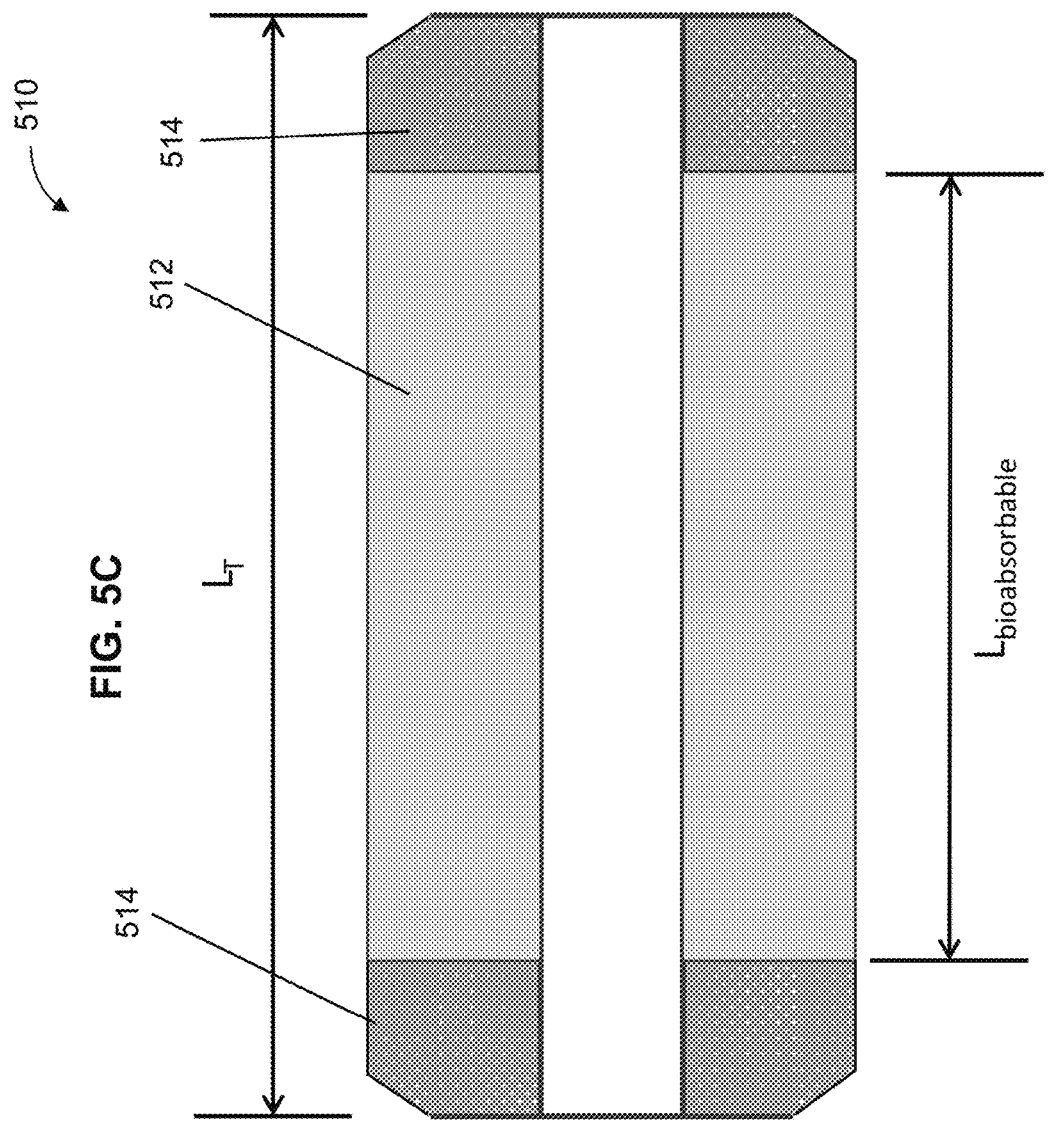

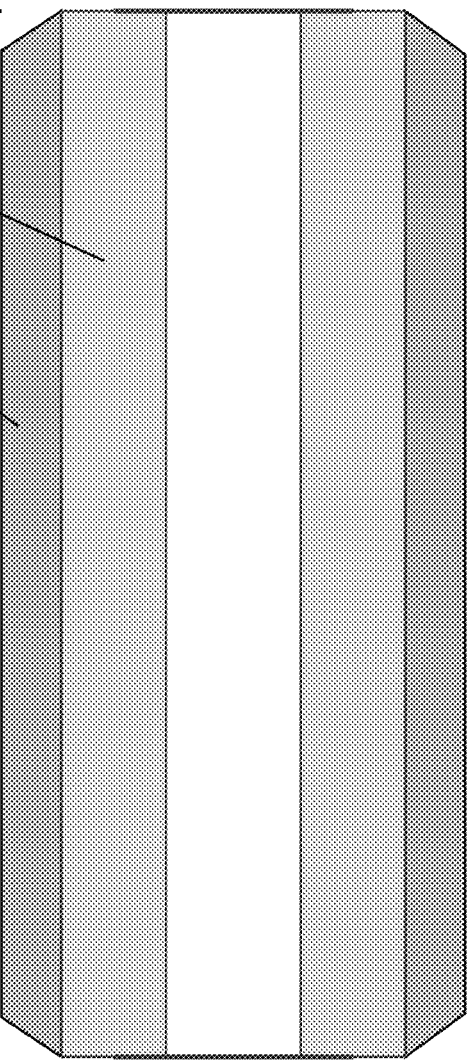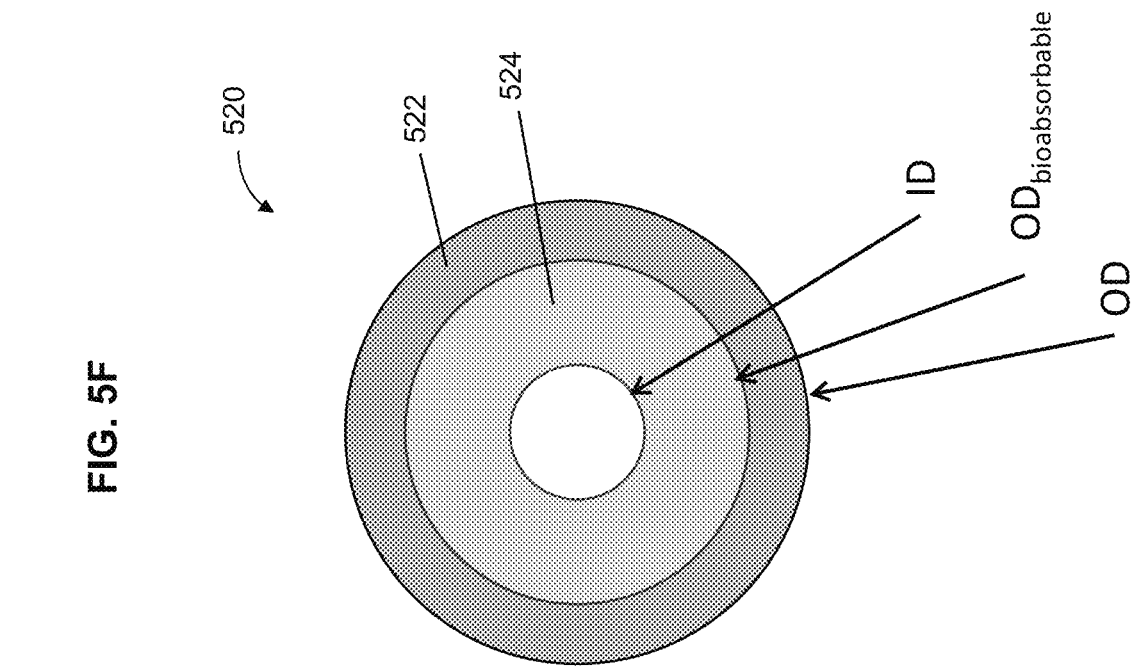
FIG. 5E
FIG. 5F

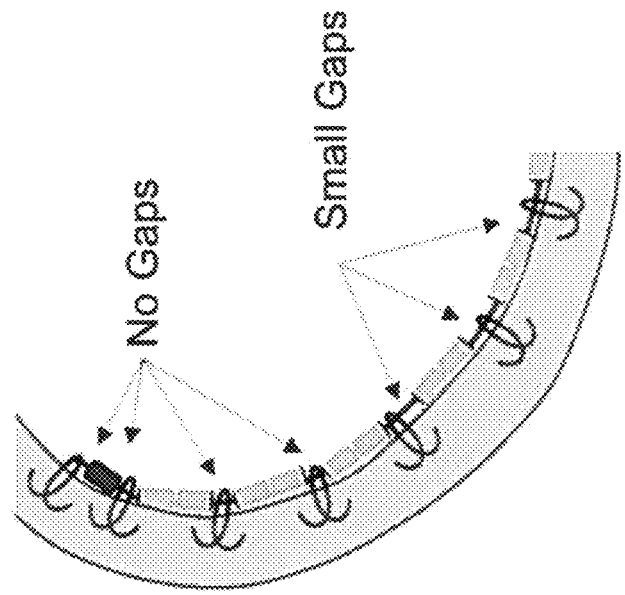
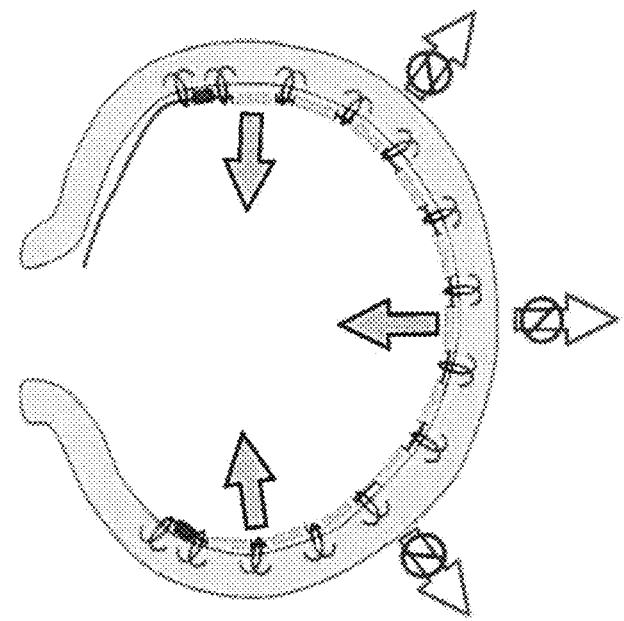
FIG. 16B
FIG. 16A

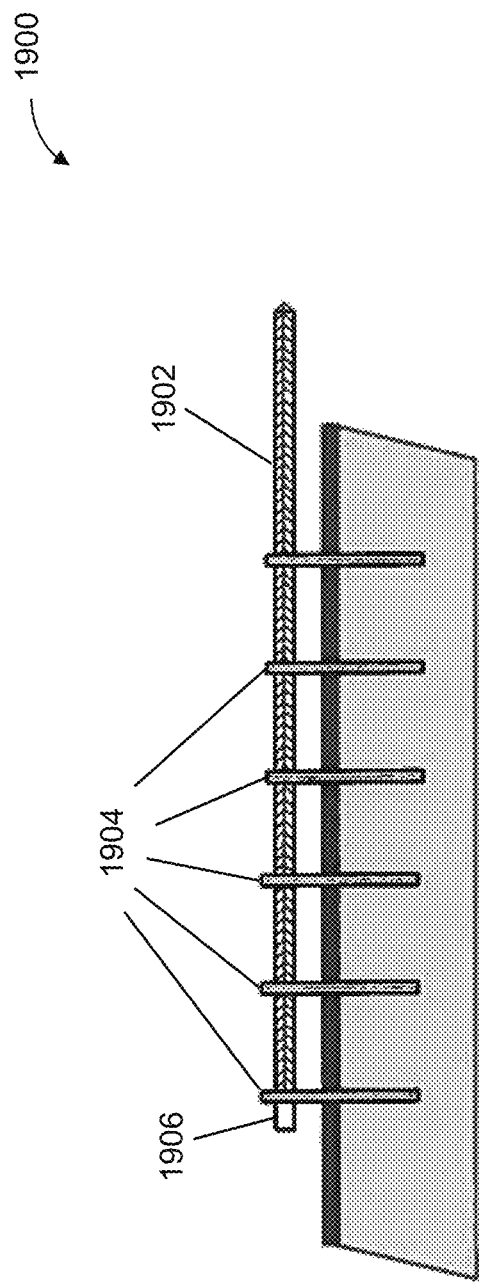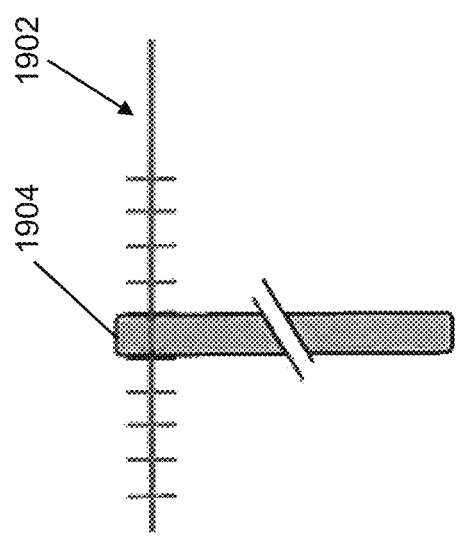
FIG. 19A
FIG. 19B

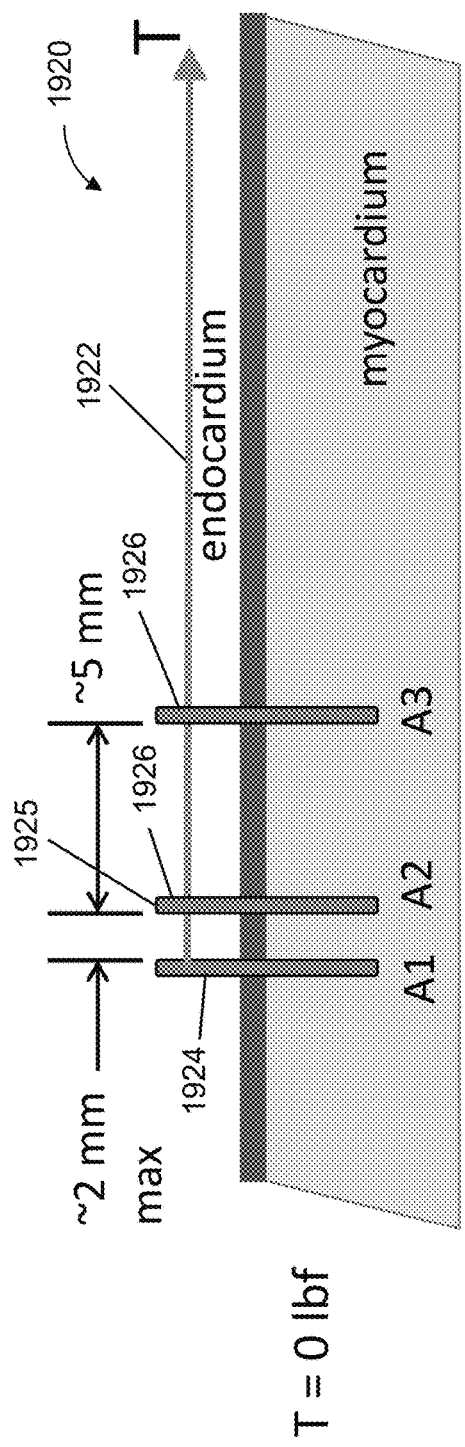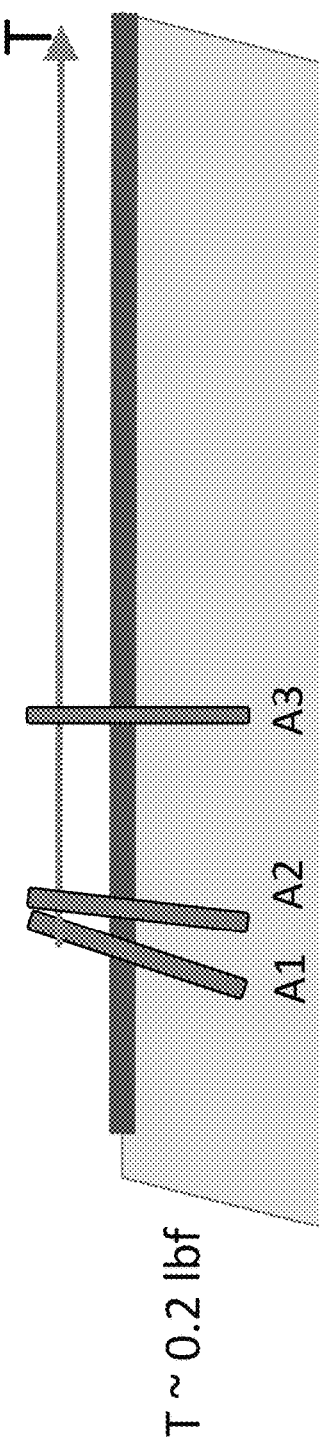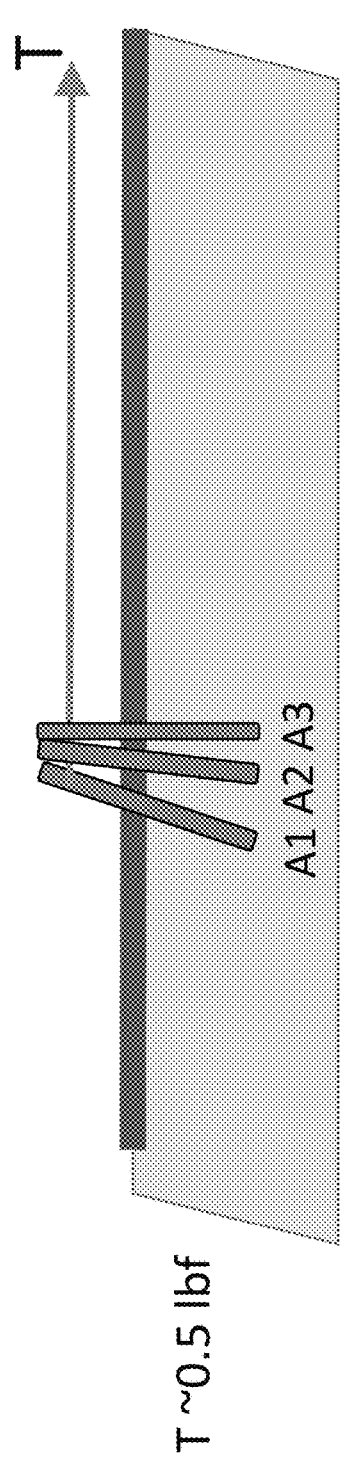

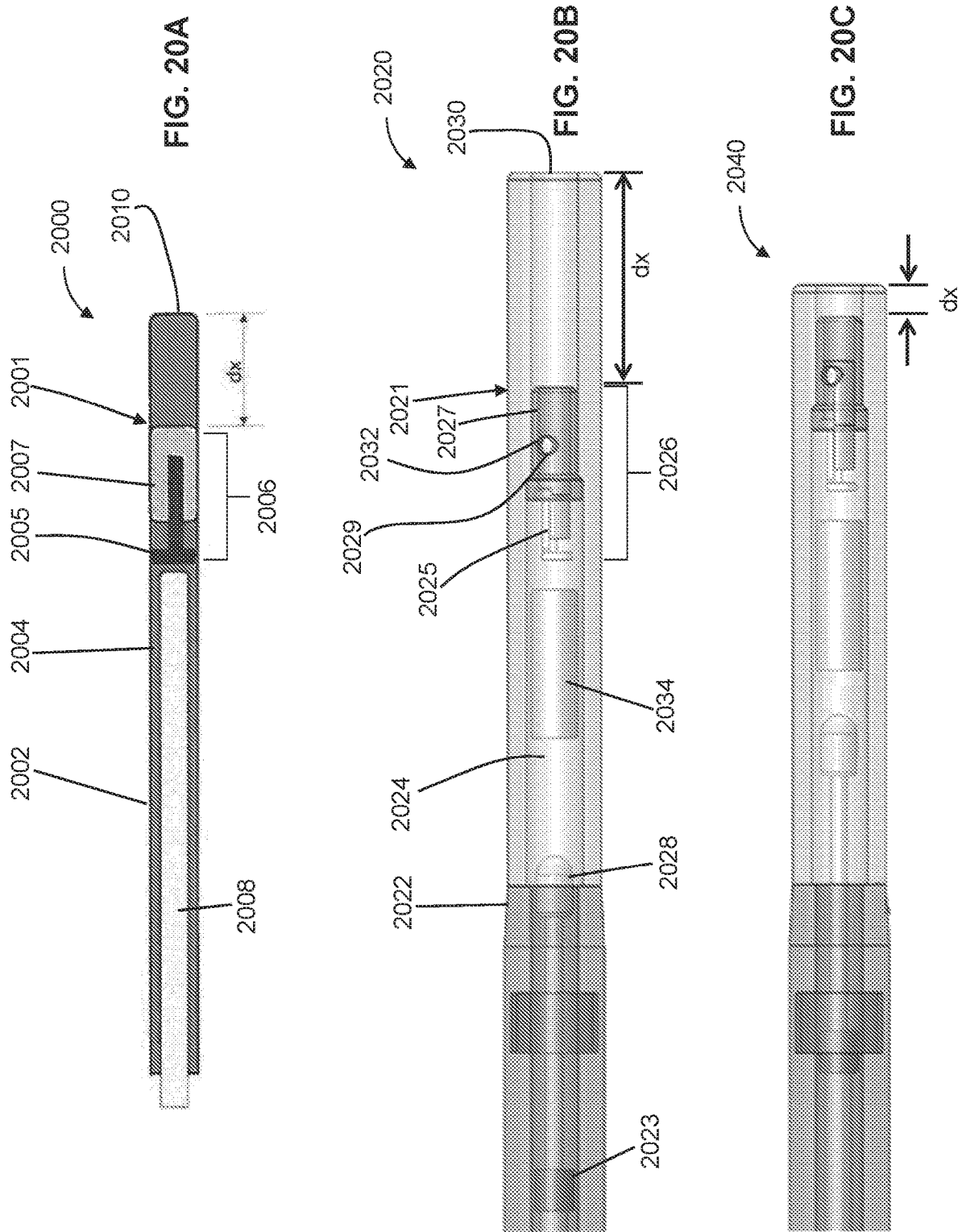

MYOCARDIAL IMPLANT LOAD SHARING DEVICE AND METHODS TO PROMOTE LV FUNCTION

CROSS-REFERENCE TO RELATED APPLICATIONS

This application claims priority to U.S. Provisional Patent Application No. 62/424,120, filed Nov. 18, 2016, which is hereby incorporated by reference in its entirety.

BACKGROUND

Many surgical therapies for functional mitral regurgitation (FMR) have been developed that treat the mitral valve (MV) annulus. Examples include the Carpentier ring annuloplasty and Kay annuloplasty procedures, which achieve annular reduction, and the Alfieri stitch, which coapts the MV leaflets using a suture. Percutaneous procedures have also been developed that adapt these surgical procedures to catheter based procedures. Each of these therapies treats only the symptoms of the underlying cardiomyopathy (e.g., mitral valve regurgitation) and not the cause (e.g., remodeling of the left ventricle).

It has been recognized that reducing the dilated left ventricle (LV) wall directly addresses the underlying cause of worsening FMR and heart failure (HF) symptoms by reducing preload and the effect of afterload—wall stress—on the LV.

Implants designed to cinch the LV free wall can also be used to address FMR. Examples include the tethered anchor implants described in U.S. Pat. Nos. 7,758,637 and 7,588,582. After gaining percutaneous access to the subvalvular space in the LV, the implant is placed against the endocardium using anchors that penetrate the myocardium and which are slidably coupled to a tether. Cinching the implant can reduce LV dimensions and volumes, improving MR status and LV function. The primary limitation to a percutaneous cinching approach in the LV is the diseased myocardium itself, which often is comprised of trabeculated (non-compacted) myocardium, post-MI scar tissue and weakened, friable myocardium. Such tissue is not well suited to withstand the loads induced by a cinched implant at the tissue-anchor interfaces.

Accordingly, there remains a need to provide a device and method to adequately place and cinch an implant into human myocardium, while not exceeding the strength of the diseased tissue.

SUMMARY

Disclosed herein are devices and methods for deploying an implant comprising a plurality of tethered anchors and force-distribution members (FDMs) to cardiac tissue to reduce the volume of a heart chamber and/or circumference of a heart valve. In some variations, one or more of the implant FDMs may be entirely or partially bioabsorbable or biodegradable. Some methods may comprise deploying the implant to cardiac tissue of a beating heart, tensioning the tether such that the implant is cinched to a "hard stop" (i.e., where further tensioning does not further cinch the implant), securing a lock member on the tether with a pre-selected length of tether between the lock member and a proximal end of the implant, and releasing the lock member to provide a pre-selected amount of slack into the implant. Alternatively or additionally, methods may comprise releasing a pre-selected amount of tension from the peak tether tension at implant hard stop (i.e., to an intermediate level of tether tension), and securing a lock member on the tether to maintain the intermediate level of tether tension. Providing a pre-selected amount of slack by releasing a pre-selected length of tether to the implant in its hard stop configuration may provide cardiac tissue with a margin for motion. When the implant is cinched to its the hard stop configuration, the anchors and FDMs may be in contact with, and/or apposed to, each other. While this may distribute load forces across multiple anchors via the FDMs, this may restrict contraction and/or expansion of the cardiac wall. When a pre-selected amount of slack is provided to the implant (e.g., by introducing a pre-selected length of tether to the implant after it has been cinched to its hard stop configuration), there may be gaps or separations between the anchors and FDMs. These gaps may provide a margin for motion, where the anchors and FDMs may be moved into contact and away from each other as the cardiac wall contracts and expands. In some variations, gaps from about 1.5 mm to about 2.5 mm between a subset of FDMs in a central portion of the implant may provide a sufficient margin for motion while still providing a reduction in the dimensions of the cardiac valve or chamber. The combination of cinching the implant to reduce the dimensions of the cardiac chamber, providing a pre-selected amount of slack to permit a controlled range of cardiac wall motion, as well distributing load forces across multiple anchors via the FDMs may help to address diseased myocardium and/or FMR. One variation of a method may comprise cinching the implant to its hard stop configuration, providing a pre-selected length of tether from about 5 mm to about 15 mm (e.g., about 9.5 mm for an implant having 14 tethered anchors and 11 FDMs between the anchors), and locking in the slack corresponding to this pre-selected length of tether.

Also disclosed herein are lock deployment catheters that are configured to secure a lock member on the tether at a pre-selected distance or offset away from the lock exit opening of the lock deployment catheter and/or proximal-most anchor of the implant in order to provide a pre-selected amount of slack to the device.

One variation of a method for tensioning and locking a tether may comprise tensioning a tether of an implant to cinch the implant to its hard stop configuration, where further tensioning of the tether does not further cinch the implant, securing a lock member on the tether with a pre-selected length of tether between the lock member and a proximal end of the implant, and releasing the lock member to provide the pre-selected amount of slack into the implant. The pre-selected length of tether may correspond to a pre-selected amount of slack. The method may also comprise loading the tether in a lock deployment catheter before tensioning the tether. The lock deployment catheter may comprise an elongate body having a longitudinal lumen therethrough that terminates at a distal-most opening, a lock member docking section located within the lumen that retains the lock member at the pre-selected distance from the distal-most opening, and a push member slidably disposed within the longitudinal lumen. The pre-selected distance may correspond to a pre-selected amount of slack applied to the implant after it has been cinched to its hard stop configuration. In some variations, the pre-selected distance may be from about 5 mm to about 15 mm, e.g., about 9.5 mm. The lock member may comprise a tube having longitudinal lumen and a side opening, and a plug slidably disposed within the lumen of the tube, and loading the tether in the lock deployment catheter may comprise loading the tether through the side opening of the tube. Securing the lock member may comprise distally sliding the push member to urge the plug into the tube to secure the lock member at the lock member docking section. The method may further comprise releasing the lock member from the lock deployment catheter.

In some variations, the implant may comprise a plurality of tethered anchors and force-distribution members located between the anchors in an alternating pattern. When the implant is in the hard stop configuration, the tethered anchors and force-distribution members may contact each other. Securing the lock member may comprise engaging the lock member on the tether at the pre-selected length away from a proximal-most anchor of the implant. The pre-selected length may be from about 5 mm to about 15 mm, e.g., about 9.5 mm. The pre-selected amount of slack may provide a gap from about 2 mm to about 3.5 mm between at least two of the plurality of force-distribution members, e.g., a gap of about 2.5 mm.

Another variation of a method for tensioning and locking a tether may comprise tensioning a tether of an implant to cinch the implant to its hard stop configuration, where further tensioning of the tether does not further cinch the implant, releasing a pre-selected amount of the tether tension to a reduced level of tension, and securing a lock member on the tether to retain the reduced level of tension in the cinched implant.

Any of the methods described herein may further comprise deploying an implant comprising a plurality of tethered anchors and force-distribution members to ventricular wall tissue in a subvalvular region of a heart.

Also described herein is a lock deployment catheter. One variation of a lock deployment catheter may comprise an elongate body having a longitudinal lumen therethrough that terminates at a distal-most opening, a lock member configured to be secured over a tether, a lock member docking section located within the lumen that retains the lock member, and a push member slidably disposed within the longitudinal lumen. The lock member docking section may be located at a pre-selected distance from the distal-most opening such that the lock member secures the tether with a pre-selected amount of slack that corresponds to the pre-selected distance. The lock deployment catheter may further comprise a tubular stop member located within the longitudinal lumen. The pre-selected distance may be from about 5 mm to about 15 mm, e.g., about 9.5 mm. The lock member may comprise a tube having a lumen and a plug configured to fit within the lumen such that the tether is secured between the walls of the plug and the tube. The lock deployment catheter may also comprise a first opening in a sidewall of the elongate body and a second opening in a side wall of the lock member tube. The first and second openings may be configured to thread a tether therethrough. In some variations, the lock member docking section may retain the lock member by snap-fit.

Also described herein are implants that may be used to tighten cardiac tissue. One variation of an implant may comprise a tether, a plurality of tissue anchors slidably coupled to the tether, and a plurality of force-distribution members coupled to the tether and each force-distribution member is disposed between a pair of tissue anchors, where at least one of the force-distribution members comprises a portion made of a bioabsorbable material. The at least one force-distribution member may be comprised entirely of the bioabsorbable material. Alternatively, the at least one force-distribution member may comprise a central portion that comprises a non-bioabsorbable material and two end portions that comprise a bioabsorbable material. The central portion may comprise, for example, nickel-titanium alloy and the two end portions may comprise, for example, PLGA (e.g., 75:25 PLGA). In some variations, the bioabsorbable material may completely dissolve in 90 days or more. Alternatively or additionally, the portion of the force-distribution member that is made of the bioabsorbable material may become structurally amorphous in 30 days or more, e.g., 90 days or more. In some variations, the plurality of tissue anchors may comprise a distal-most terminal anchor that is fixedly coupled to the tether, a plurality of intermediate anchors and a proximal-most terminal anchor that are slidably coupled to the tether. The plurality of force-distribution members may be located between the plurality of intermediate anchors. The force-distribution members may be tubular. Optionally, any of the force-distribution members may comprise a bioabsorbable material that may comprise a drug-eluting material. In some variations, a force-distribution member located between the distal-most terminal anchor and a next-to-distal-most anchor may be made of a non-bioabsorbable material, a force-distribution member located between the proximal-most terminal anchor and a next-to-proximal-most anchor may be made of a non-bioabsorbable material, and a force-distribution member located between two intermediate anchors may comprise a bioabsorbable material.

BRIEF DESCRIPTION OF THE DRAWINGS

FIG. 1C and FIG. 1D depict a slidably coupled implant placed in the myocardium of the LV in the uncinched and cinched conditions, respectively.

FIG. 1E demonstrates the cinchable implant preventing distension of the LV. FIG. 1F demonstrates that the cinchable implant does not restrict contraction during systole.

FIG. 5A is a side cross-sectional view of one variation of a FDM. FIG. 5B is an end view of the FDM of FIG. 5A. FIG. 5C is a side cross-sectional view of one variation of a FDM. FIG. 5D is an end view of the FDM of FIG. 5C. FIG. 5E is a side cross-sectional view of one variation of a FDM. FIG. 5F is an end view of the FDM of FIG. 5E.

FIG. 16A depicts a cinched implant with slidably coupled anchors and FDMs, in which gaps remain. FIG. 16B presents a detailed view of the cinched implant with gaps, depicting the gap locations.

FIG. 19A depicts a cinchable implant incorporating a barbed suture as the tether, placed inside a flexible polymer extrusion.

FIG. 19B depicts a detail view of an implanted anchor fixed to the barbed suture after the flexible polymer has been removed.

FIGS. 19D-19F depict one variation of an implant with increasing levels of tension on the tether.

FIG. 20A depicts one variations of the distal end of a lock deployment catheter, showing the lock, push tube, and an offset distance (dx) between the catheter distal tip and the lock distal tip. FIG. 20B depicts a side view of a rendering of one variation of a lock deployment catheter with an offset distance (dx). FIG. 20C depicts a side view of a rendering of another variation of a lock deployment catheter with an offset distance (dx) that is less than the offset distance of the variation depicted in FIG. 20B.

DETAILED DESCRIPTION

Figure 1B:
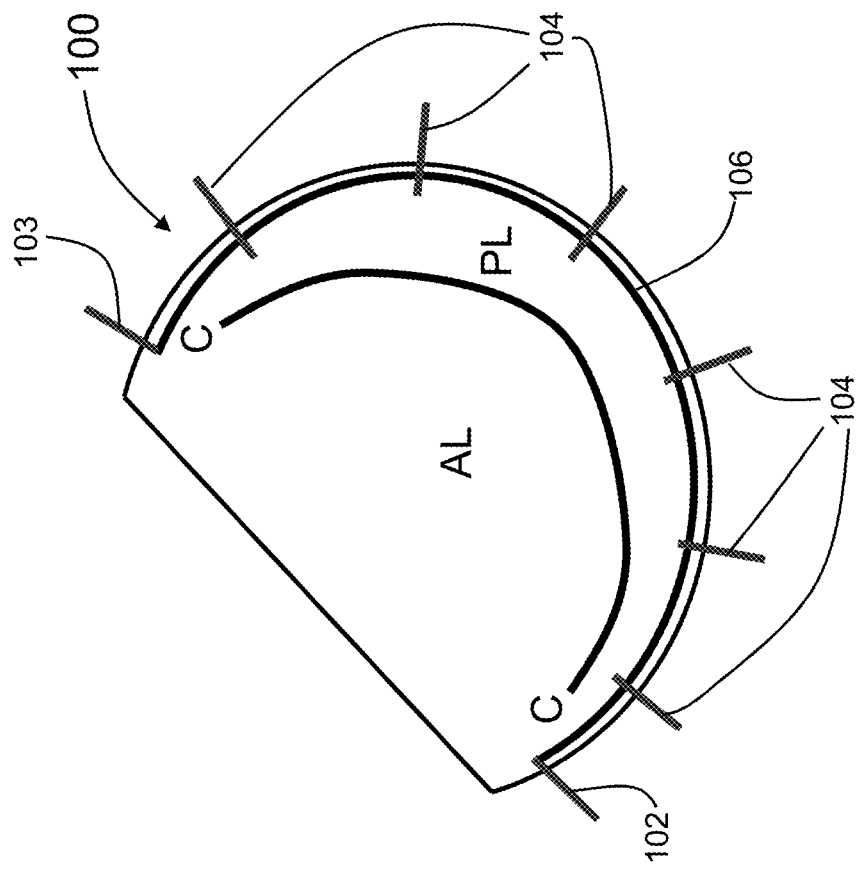
FIG. 1B is a schematic view of the mitral valve from FIG. 1A with an implant.

Disclosed herein is an improved implant capable of being cinched to reduce LV wall dimensions, while also accommodating inherent weakness in diseased human myocardium. In one variation, the implant may comprise a tether, a plurality of anchors slidably coupled to the tether, and one or more bioabsorbable force distribution members (FDMs) or tubular links slidably coupled to the tether between two or more of the anchors. The FDMs may be entirely or partially bioabsorbable or biodegradable. The rate of absorption or degradation of the entire or portion of the FDM may correspond with the rate at which the implant is incorporated and/or covered by cardiac tissue (e.g., pannus tissue). For example, the FDMs may comprise one or more bioabsorbable or biodegradable materials that absorb or degrade in about 90 days, which may be about the same amount of time for the implant to be incorporated into surrounding cardiac tissue. For example, the FDMs may comprise PLGA, and the ratio of lactic-to-glycolic acid may be selected to obtain the desired degradation rate (e.g., FDMs comprising 75:25 PLGA may biodegrade or bioabsorb in about 90 days).

Also disclosed herein are methods for delivering the implant, tensioning the tether to cinch the implant to a hard stop or peak tension level (e.g., where further tensioning of the tether does not further cinch the implant, and/or where substantially all the anchors and adjacent FDMs are in contact with each other and/or intervening cardiac tissue), and engaging a lock member on the tether such that a pre-selected amount of slack is provided to the implant. A pre-selected amount of slack may be provided by releasing a pre-selected length of tether after the implant has been cinched to its hard stop configuration. For example, the pre-selected length of tether may be introduced to the implant at a proximal-most end anchor, and as the heart continues to beat, the slack provided by the additional length of tether may migrate to the intermediate anchors and FDMs (e.g., in the center portion of the implant). Introducing a gap or separation between intermediate FDMs may allow for an increased range or margin of motion in the central portion of the implant, but still constrain the dimensions of the valve or chamber. The pre-selected amount of slack may allow the cardiac wall to expand and contract without further damaging surrounding tissue. In some variations, the pre-selected length of tether introduced after the implant has been cinched to its hard stop configuration may be from about 5 mm to about 15 mm, e.g., about 9.5 mm, about 10 mm. The gap or separation between intermediate FDMs may be from about 1.5 mm to about 3.5 mm, e.g., about 2.5 mm. For example, locking an implant comprising 14 tethered anchors and 11 FDMs located between the anchors with a tether length of about 9.5 mm from its hard stop configuration may provide a level of slack that promotes desirable cardiac remodeling. Some methods may comprise the use of a locking catheter that comprises a lock member docking section that is offset from the distal-most end of the catheter, where the length of the offset (e.g., the distance between the docking section and distal-most end of the catheter) corresponds to a pre-selected amount of slack that is desired. For example, the lock member docking section may be from about 5 mm to about 15 mm from the distal-most end of the catheter, e.g., about 5 mm, about 5.5 mm, about 7 mm, about 9 mm, about 9.5 mm, about 10 mm, etc. This may help facilitate the introduction of a consistent amount of slack to the implant by securing the lock member on the tether with a pre-selected length of tether between the lock member and a proximal end of the implant that corresponds to the desired level of slack.

Figure 1A:
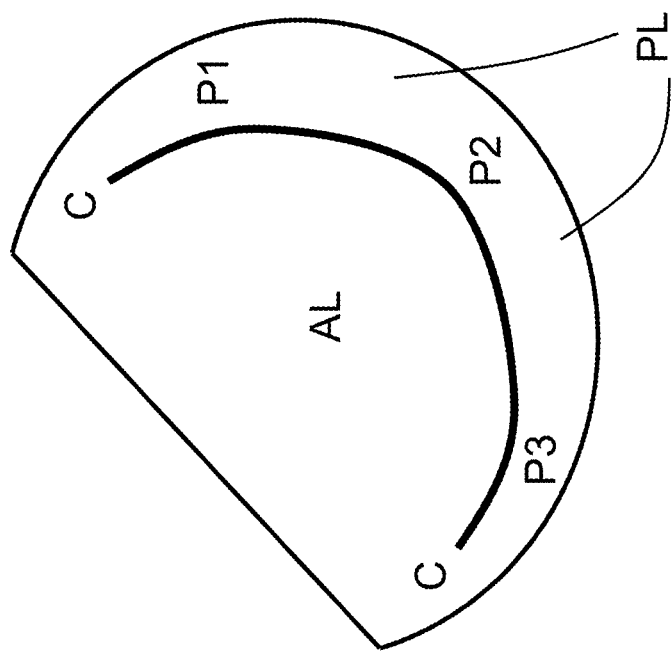
FIG. 1A is a schematic view of the mitral valve from the left ventricle.

A representative schematic view of the mitral valve from the left ventricle (e.g., from the ventricular perspective or short axis view) is provided in FIG. 1A. The mitral valve has an anterior leaflet AL and a posterior leaflet PL that has three scallops P1-P3 (e.g., a lateral scallop, a central scallop and a medial scallop). The anterior leaflet and posterior leaflet converge at the posteromedial and anterolateral commissures C. One example of an implant comprising a plurality of tethered anchors that may be deployed to the ventricular wall tissue below the mitral valve (e.g., tissue within a subvalvular space) is schematically depicted in FIG. 1B. The implant (100) may comprise a plurality of anchors that are coupled to a tether (106), where the distal-most terminal or end anchor (102) is fixedly coupled to the tether (e.g., a distal-most anchor) and the intermediate anchors (104) and a proximal-most terminal or end anchor (103) are slidably coupled to the tether. The implant may be deployed and attached to ventricular wall tissue surrounding the mitral valve. Cinching the implant (100) may help to reduce the volume of the LV and counteract the effects of a dilated LV. FIGS. 1C-1F depict the implant (100) deployed and attached to ventricular wall tissue (108) in a subvalvular space of the mitral valve. FIG. 1C depicts the implant (100) attached to a free wall of the LV, located between the annular plane and papillary muscle insertion, in an untensioned state. In some variations, the implant may be deployed an attached to ventricular tissue and may circumscribe the annulus of the mitral valve, or may extend around a portion or arc of the annulus. As shown in FIG. 1D, tensioning the tether (106) may cinch the implant (100), drawing the anchors closer together to cause a reduction in LV dimensions and volumes. This may help to improve MR grade and LV functional status. Once the slack has been removed from the tether and the device is locked in this tensioned state, the LV cannot distend beyond the size the implant allows during diastole (FIG. 1E). That is, the implant resists expansion of the ventricular wall. During systole, however, the LV can continue to contract toward end systole (FIG. 1F). In other words, the implant (100) is non-distensible but is flexible and contractible.

Figure 2A:
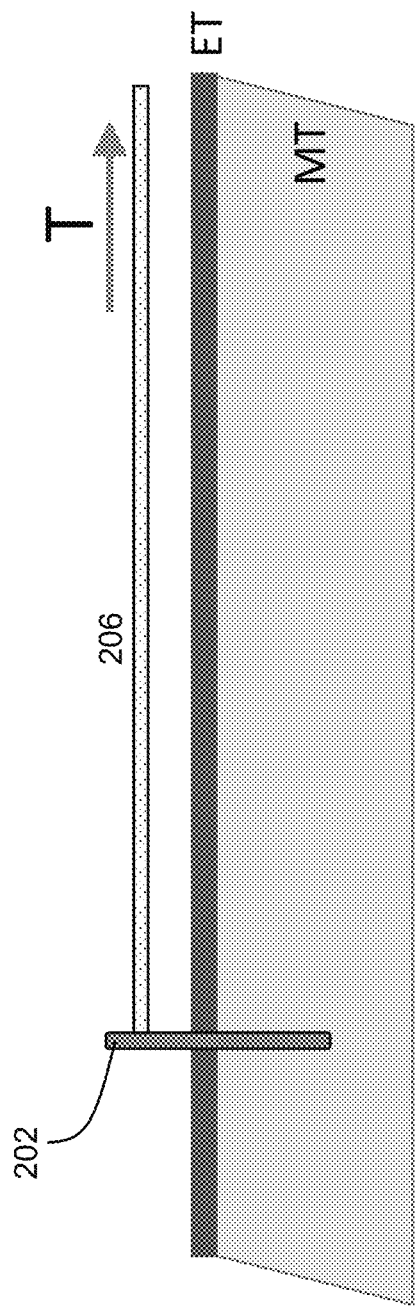
FIG. 2A depicts an end anchor of an implant, attached to a tether under tension.
Figure 2B:
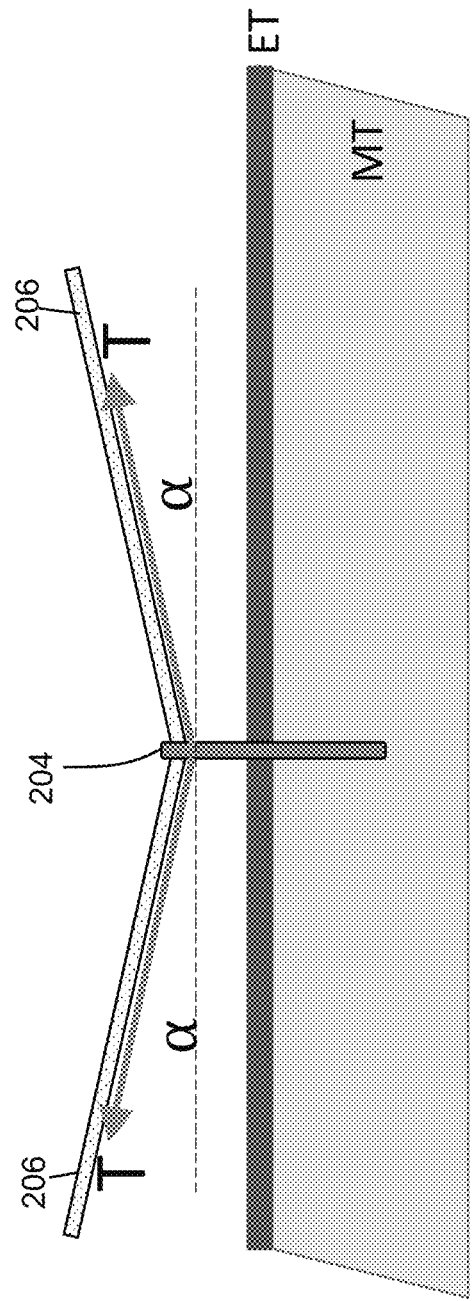
FIG. 2B depicts an intermediate anchor of an implant, slidably coupled to a tether under tension.

One limitation to this previously-developed implant and cinching approach in the LV is the diseased myocardium itself, which often is comprised of trabeculated (non-compacted) myocardium, post-MI scar tissue and weakened, friable myocardium. Such tissue is not well suited to withstand the loads induced by a cinched implant at the tissue-anchor interfaces. This is particularly true at the two ends of the implant, where the loads may be greater in magnitude and tangential in direction compared to the intermediate points of the implant where loads may be radially oriented and lower in magnitude. FIG. 2A depicts a cross-sectional view of myocardial tissue MT with an end anchor (202) of a tethered-anchor implant device attached or implanted into endocardial tissue ET and MT. The end anchor (202) may be fixedly attached to a tether (206), which may be subjected to a proximally-directed force that places the tether (206) under tension T. The entire magnitude of tension T may be reacted at the anchor-tissue interface in a direction parallel to the endocardial surface. FIG. 1B depicts the same tissue with an intermediate anchor (204) slidably coupled to the tether (206) under tension T. The net force reacted at the anchor-tissue interface may be radial in direction, with a magnitude of $2T(\sin \alpha)$. For smaller values of angle $\alpha$ (i.e., the distance between anchors is appropriately limited), this reacted force may be reduced.

Figure 3A:
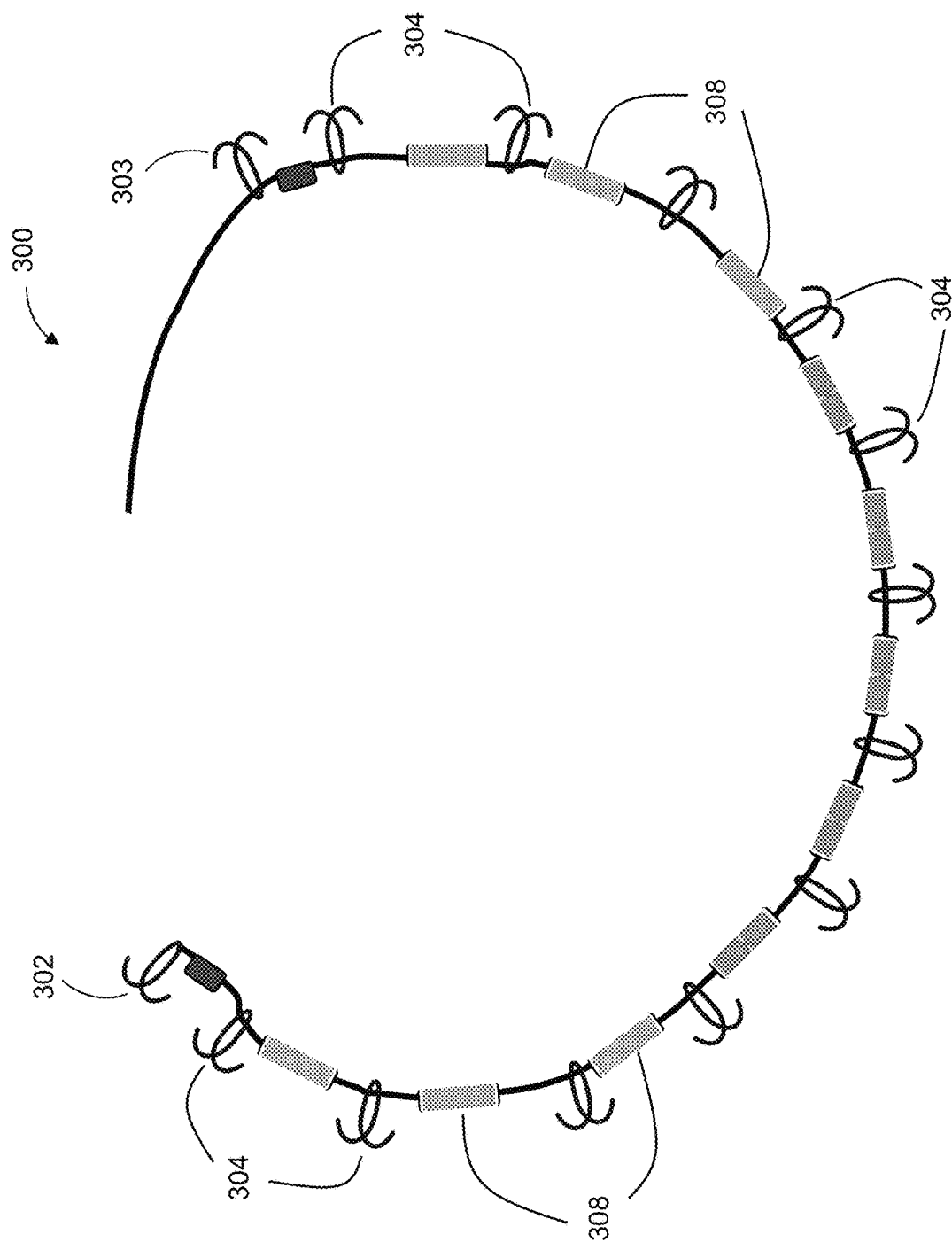
FIG. 3A is a schematic depiction of one variation of an implant.
Figure 3B:
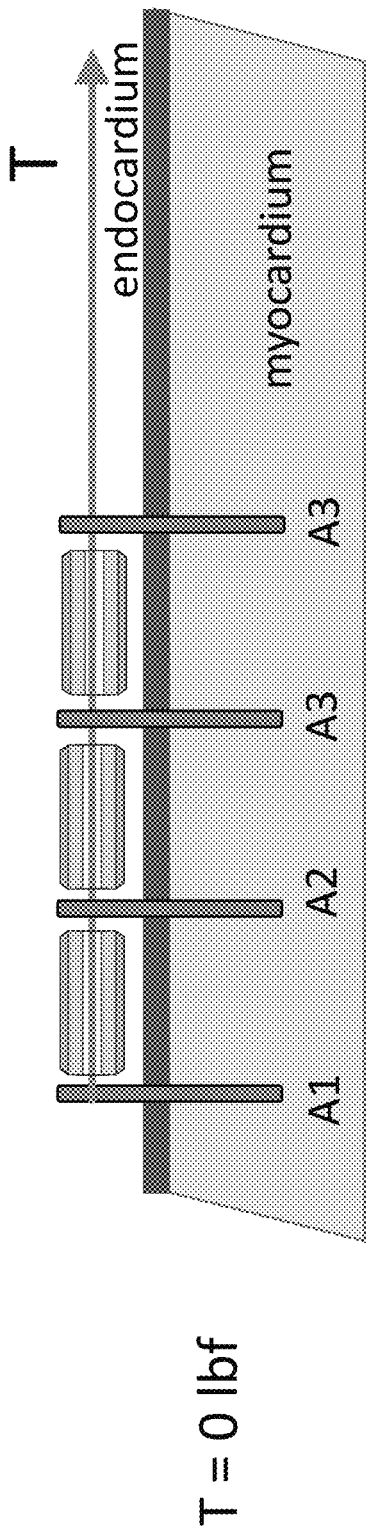
FIG. 3B is a side cross-sectional view of a portion of the implant of FIG. 3A.
Figure 3C:
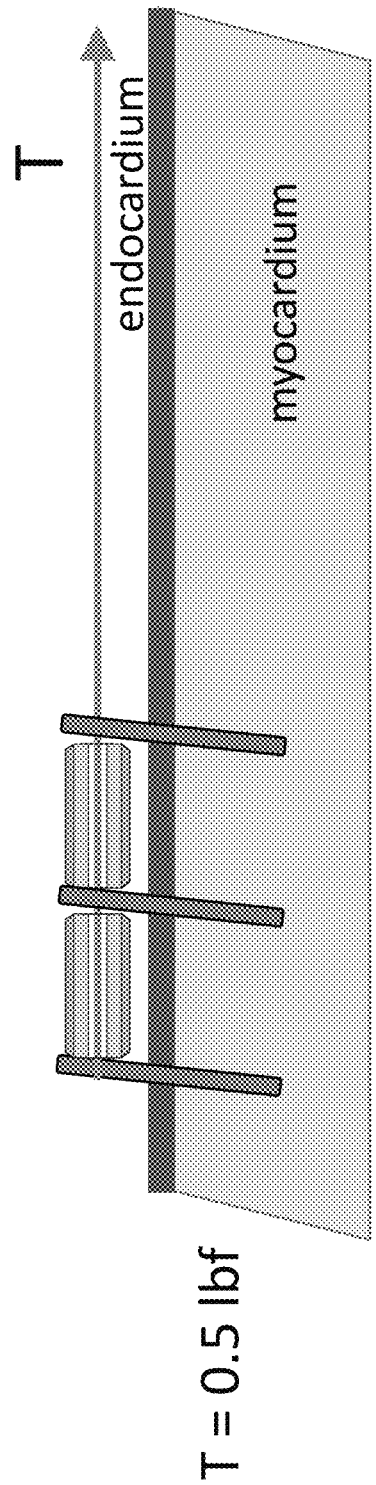
FIG. 3C is a side cross-sectional view of the implant of FIG. 3B with tension applied.

The devices described herein may help to reduce or limit the forces reacted at the anchor-tissue interface. FIG. 3A depicts one variation of an implant (300) comprising a tether (306), a plurality of tissue anchors (304) slidably coupled to the tether, one or more FDMs or tubular anchor links (308) slidably coupled to the tether and located between each of the tissue anchors. The FDMs may couple the anchors together after the implant has been cinched to a certain amount (e.g., by applying a certain amount of tension applied to the tether). The amount of implant cinching (and therefore tissue tightening) that may be achieved may be a function of the distance between anchors in the uncinched implant and the length of the FDMs. FIG. 3B is a side cross-sectional view of a portion of the implant of FIG. 3A deployed and attached to tissue before tension is applied (T=0 lbf) to the tether. FIG. 3C is a side cross-sectional view of the implant of FIG. 3B with tension applied (T=~0.5 lbf) to the tether. The FDMs between the anchors A1-A3 prevent the anchors from being drawn too closely to each other (i.e., they cannot be drawn closer than the length of the FDM, without injuring the tissue). The distal-most terminal or end anchor (302) (e.g., the first anchor implanted into tissue) may be fixedly attached to the tether (306). While in some variations the proximal-most terminal or end anchor (303) (e.g., the last anchor of the implant implanted into tissue) may be slidably coupled to the tether (306), in other variations, the proximal-most end anchor may be fixedly attached to the tether (e.g., by knotting, crimping, adhesion, and the like). The FDMs (308) may be partially or completely bioabsorbable or biodegradable. After the implant (308) is deployed and the anchors are inserted into the desired cardiac tissue (e.g., ventricular wall tissue at or near a valve region or subannular region, left ventricular wall tissue at or near the subannular region of a mitral valve), tension may be applied to the tether (306), reacted at the proximal-most end anchor (303) to cinch the implant and reduce the volume of the ventricle and/or circumference of the valve. Tension may be applied to the tether in order to cinch the implant down to a hard stop, where the tissue anchors and FDMs are in apposition to each other. in some variations, when the implant is cinched into the hard stop configuration, variabilities in the implantation depth of the tethered anchors may be reduced. For example, anchor that have been implanted at a greater depth into tissue may be urged to the surface of the tissue when the implant has been cinched to its hard stop configuration. After the implant has been cinched to its hard stop configuration, and a pre-selected amount of slack (or reduction in tension from this peak level of tension) may be provided and locked onto the implant. The pre-selected level of slack or tension reduction from the peak tension level may be provided by introducing a pre-selected length of tether to the implant after it has been cinched to its hard stop configuration. Providing a pre-selected level of slack may allow the cardiac tissue to contract and expand as the heart beats without injuring or further damaging the cardiac tissue. The lengths of the FDMs along the implant may vary depending on the desired force distribution and/or whether localized areas of additional tissue cinching may be desired. For example, for cardiac regions where additional cinching may be desired, the FDMs of the implant delivered to those regions may be shorter in length than FDMs of the implant delivered to other regions for which less cinching is indicated. In some variations, the FDMs between the terminal anchor and the next-to-terminal anchor may have a shorter length than the FDMs between intermediate anchors.

FDMs may be made of one or more biodegradable or bioabsorbable materials. In some variations, one or more FDMs may be made entirely of biodegradable or bioabsorbable materials. Alternatively or additionally, one or more FDMs may be a composite of bioabsorbable structures and non-bioabsorbable structures. For example, a central portion of a FDM may be made of a non-bioabsorbable material while the end portions of the FDM may be made of a bioabsorbable material so that over time, the overall length of the FDM shortens as the ends biodegrade. In some variations, an outer portion or layer of the FDM may be made of bioabsorbable materials while the inner portion of the FDM may be made of a non-bioabsorbable material. The absorption rate of the bioabsorbable portions may be selected to coincide with the rate at which the implant is incorporated into cardiac tissue.

While the devices and methods described below are in the context of addressing LV remodeling and/or MV regurgitation, it should be understood that these devices and methods may also be used to mitigate the effects of heart failure and/or or tricuspid regurgitation in cardiac regions such as the right ventricle.

Systems

Anchors

Figure 4C:
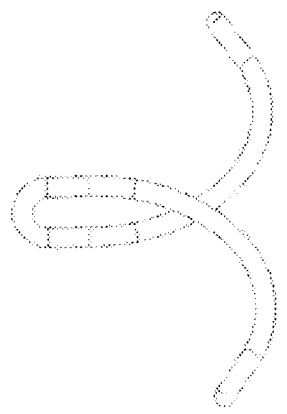
FIGS. 4A-4H depicts variations of tissue anchors.
Figure 4B:
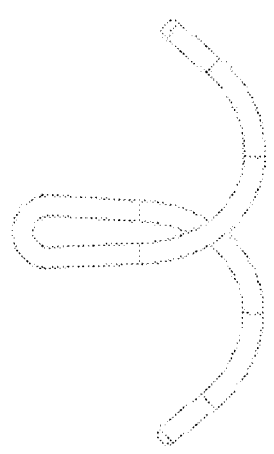
Figure 4A:
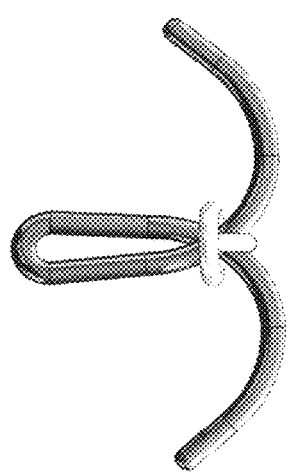
Figure 4F:
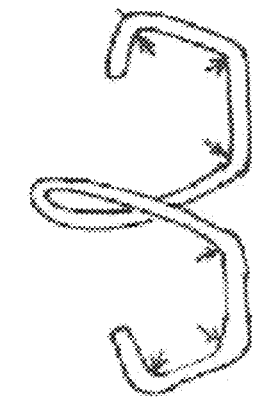
Figure 4E:
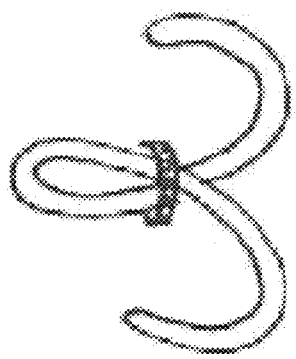
Figure 4D:
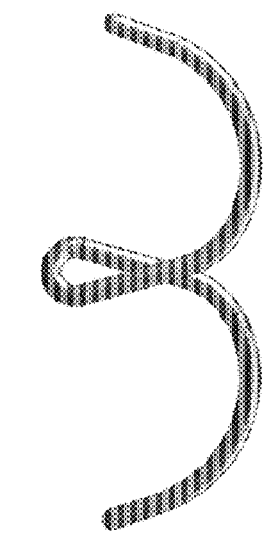
Figure 4H:
Figure 4G:
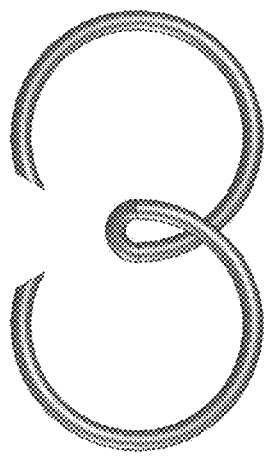

The implant may comprise any number of tissue anchors as may be desired. FIGS. 4A-4H depicts various tissue anchors formed from a single wire body that may be included in any of the implants described herein. FIGS. 4A-4G depict anchors in their deployed, tissue-piercing configurations while FIG. 4H depicts an example of an anchor in an undeployed, stowed configuration. The tissue anchors may comprise a tissue attachment portion and an eyelet or loop portion that is configured for retaining a tether therethrough. The tissue attachment portion may comprise a first leg and a second leg, each leg having a tissue-piercing end for penetrating cardiac tissue, and one or more curves along the length of each leg to engage cardiac tissue. Optionally, some tissue anchors may comprise a ring-shaped wire or collar at the base of the eyelet or loop that reinforces the size and shape of the loop. The eyelet or loop may have an elongate shape and/or a narrow profile that tapers to the base, which may facilitate tissue penetration. The anchor (either or both the tissue attachment portion and the eyelet or loop portion) may be made of an elastic material (e.g., a super-elastic material) and/or a shape-memory material. Examples of such materials may include any metals, alloys, such as nickel titanium alloy (Nitinol), or polymers (e.g., rubber, poly-ether ether ketone (PEEK), polyester, nylon, etc.). FIG. 4A depicts one variation of an anchor comprising an elongate eyelet (e.g., where the length of the eyelet is at least twice its width), two tissue-penetrating legs extending from the base of the eyelet, and a ring-shaped wire or knot secured at the base of the eyelet. The anchor may be made of a single, continuous wire (e.g., of nitinol) that extends in a single-turning direction from one end to the other end, forming a loop in between the ends. The shape and size of the loop may be secured with the knot. The eyelet has a constant taper or narrowing from the top to the base as the two sides extend to the base and crossover to form the legs. FIG. 4B depicts another variation of an anchor that is similar to the anchor in FIG. 4A, but without the ring-shaped wire or knot at the base of the eyelet. FIG. 4C depicts another variation of a tissue anchor comprising an elongate eyelet and two tissue-penetrating legs extending from the base of the eyelet, but the sides of the eyelets may be parallel to each other so that the central portion of the eyelet has a constant width. The taper or narrowing of the eyelet or loop may be closer to the base of the eyelet as compared to the anchors depicted in FIGS. 4A and 4B. FIG. 4D depicts another variation of an anchor where the length of the eyelet is relatively short as compared to the width of the eyelet (e.g., the length is less than twice the width of the eyelet). The length and curvature of the legs extend further from the eyelet than the anchors of FIGS. 4A-4C, which may facilitate tissue attachment. FIG. 4E depicts one variation of an anchor comprising a collar at the base of the eyelet and two legs that curve inward. FIG. 4F depicts one variation of an anchor where the legs are made up or a plurality of straight segments. The leg ends point back toward the eyelet. FIG. 4G depicts another example of a tissue anchor where the legs ends are sharpened and extend over the top of the eyelet and also point back toward the eyelet. The radius of curvature of the leg curves is less than the radius of curvature of the legs in the anchors of FIGS. 4A-4G. FIG. 4H depicts the undeployed, compressed configuration of the anchor of FIG. 4G. The undeployed, compressed configuration for the anchors of FIGS. 4A-4G may generally have a narrower profile than in the deployed configuration, which may facilitate catheter-based anchor delivery. The eyelet of the anchor in FIGS. 4G-4H may change its size and/or shape as it transitions from the undeployed configuration to the deployed configuration (e.g., the length of the eyelet may reduce as the anchor transitions from the undeployed to deployed configuration). Alternatively, the eyelet of the anchor may be substantially the same in both the undeployed and deployed configurations. For example, the eyelet of the anchors depicted in FIGS. 4A-4C and 4E may remain substantially same size and shape, but the curvature of the legs may change from a relatively straight configuration before deployment to a curved configuration after deployment in order to engage tissue. The implants described herein may comprise anchors that are all be the same type (e.g., all the anchors in the implant may be the anchor depicted in FIG. 4A), or may comprise anchors of different types in any combination (e.g., terminal anchors may have the collar at the base of the loop while intermediate anchors may not have a collar). Additional description of various anchors that may be used is provided in U.S. Pat. Appln. Pub. No. 2012/0271331 and U.S. Pat. Appln. Pub. No. 2014/0148849, the disclosures of which are hereby incorporated by reference in their entirety.

Force-Distribution Members (FDMs)

Force-distribution members for the implants may comprise a cylindrical or tubular structure with a central lumen that extends along its longitudinal axis, terminating at two openings on the ends of the tubular structure. The lumen may have a diameter that is wide enough for a tether to pass through and for the FDM to slide along the tether. In some variations, a FDM may have a length from about 3 mm to about 10 mm, e.g., about 0.16 in, about 0.26 in. The length may vary depending on the desired force distribution profile (e.g., shorter FDMs for areas where tighter cinching or greater volume reduction is desired. The diameter of a FDM may be from about 1 mm to about 3 mm, e.g., about 2 mm, about 0.08 in. The lumen may have a diameter from about 0.25 mm to about 0.45 mm, e.g., about 0.35 mm, about 0.032 in. In some variations, the ends of the cylindrical or tubular structure may be rounded or radiused. The surface of the FDM may be textured and/or be coated. For example, the surface of the FDM may have a pattern of cutouts and/or ridges, which may help facilitate integration with cardiac tissue. Optionally, the internal surface of the lumen (through which a tether may pass) may have a lubricious coating (e.g., polytetrafluoroethylene (Teflon), silicones, hydrophilic lubricious coatings, etc.) to help minimize friction between the FDM and the tether. The external surface of the FDM may optionally comprise surface treatments, including texturing (e.g., by ion beam etching, photoetching, etc.), tempering (e.g., thermal or photo tempering), or the like. Additional examples of appropriate surface treatments may include electropolishing, chemical etching, grit or bead blasting, and tumbling in abrasive or polishing media. Polymer coatings or coverings such as a braided or woven material, may include Teflon or polyester (e.g., PET). One or more portions of a FDM may comprise a radiopaque material, such as barium sulfate. The radiopaque material may be distributed throughout the FDM and/or may be concentrated at particular regions or bands on the FDM, as may be desirable. An implant may comprise from about 9 to about 15 FDMs, depending on the number of tissue anchors (which may be from about 10 to about 16 FDMs). For example, an implant may comprise about 9 FDMs, 11 FDMs, 13, FDMs, 15 FDMS, etc.

A FDM may be made entirely of bioabsorbable or biodegradable materials, entirely of non-bioabsorbable or non-biodegradable materials, or may be a composite structure where some portions are bioabsorbable or biodegradable and some portions are not. Although the variations of FDMs described herein may be described as comprising a bioabsorbable material or bioabsorbable component(s), it should be understood that FDMs may alternatively or additionally comprise a biodegradable material or component(s). Examples of bioabsorbable materials may comprise polymers such as poly(lactic-co-glycolic acid) or PLGA, polylactic acid (e.g., PLLA, PDLLA), and/or caprolactone polymers, PDS compounds, and/or several types of collagen from human, bovine, porcine or ovine sources that can be formed into compacted solids, and the like. The relative proportion of (or ratio between) the different monomers of a polymer may be selected to attain a desired degradation rate and/or desired mechanical properties. For example, the ratio of lactic-to-glycolic acid in a PLGA may be adjusted to attain a desired degradation rate. Some variations of FDMs may comprise a 10:90 PLGA lactic-to-glycolic acid ratio or a 85:15 PLGA lactic-to-glycolic acid ratio (e.g., from at least about a 10:90 PLGA to about a 85:15 PLGA, a 50:50 PLGA, 75:25 PLGA). Bioabsorbable materials that degrade in about 1 month to about 4 months may be used. For example, the ratio of lactic-to-glycolic acid may be selected such that the degradation rate is on the order of about 3 months or 90 days, which has been experimentally measured to be the amount of time it generally takes for an implant to be incorporated or covered by cardiac tissue. In some variations, tissue anchors and FDMs may begin to fix into tissue within days of implantation, such that a desirable degradation or absorption time is from about 2 weeks to about 4 weeks, rather than the more typical 6 to 12 months or more for bioabsorbable materials used in medical applications. The bioabsorbable material may be configured to sustain a compression load of about 1.5 lbf, with transient compressive loads of up to about 3 lbf for about 10 minutes, a radial component load of about 1 lbf, and/or may be configured to retain compressive strength for about 2 weeks. One or more of the materials may comprise a radiopaque materials, such as barium sulfate. For example, barium sulfate may be combined with the bioabsorbable material so that any portion of the FDM made of the barium sulfate doped bioabsorbable material can be visualized using fluoroscopy. Some FDMs may also comprise a drug-eluting material or layer. For example, an FDM may include pits, slots, bumps, holes, etc. for elution of drugs, or to allow tissue ingrowth. Alternatively or additionally, some portions of the FDM may be made of a non-bioabsorbable material, such as a metal alloy (e.g., nickel titanium alloy, etc.).

Optionally, FDMs may be covered by polyester or other material that helps induce tissue formation and incorporation such that shortly after implantation, the implant may become completely incorporated into the LV wall. In some variations, FDMs may optionally comprise therapeutic compounds or agents that can be delivered to the heart. In some variations, FDMs may be configured to deliver long term therapy by drug elution, cell therapy, delivery of biologics, and other medications. Any of the FDMs described herein may optionally comprise a therapeutic material (e.g., a medicinal material such as an anti-inflammatory, an anticoagulant, an antiproliferative, a pro-proliferative, a thrombo-resistant material, a growth hormone, etc.) to promote healing. For example, the FDMs may be coated with Vascular Endothelial Growth Factor (VegF), Fibroblast Growth Factor (FGF), Platelet-Derived Growth Factor (PDGF), Transforming Growth Factor Beta (TGFbeta, or analogs), insulin, insulin-like growth factors, estrogens, heparin, and/or Granulocyte Colony-Stimulating Factor (G-CSF). For example, one of the limitations in cardiac cell therapy is early cell death of injected cells, and the cells being flushed from the system. FDMs may be configured to encapsulate and nourish cells until FDMs are incorporated into the myocardium, then release the cells into the surrounding myocardium. FDMs may be seeded with, for example, endothelial cells, cardiac precursor cells, and the like.

The FDMs described herein may be manufactured using any suitable method. For example, FDMs may be injection molded, micro molded, chemically cross-linked, mechanically pressed and the like. FDMs may also be made using solid freeform fabrication techniques.

FIGS. 5A-5B depict one variation of a FDM (500) that is made of a single material, such as a completely bioabsorbable material, a non-bioabsorbable material, or a drug-eluting material. FIG. 5A is a longitudinal cross-sectional view and FIG. 5B is an end view of the FDM. For example, the entire body of the FDM may be made of a bioabsorbable material, such as 75:25 PGLA or any of the other bioabsorbable materials described above. Alternatively, the entire body of the FDM may be made of a non-bioabsorbable material, such as nitinol, and/or a drug-eluting material. FIGS. 5C-5D depict one variation of a FDM (510) where a central portion or length (512) of the FDM tubular body is made of a non-bioabsorbable material and/or a drug-eluting material, while the end portions or regions (514) of the tubular body are made of a bioabsorbable material. The FDM (500) may have a length (L) from about 3 mm to about 10 mm, may have an outer diameter (OD) of about 2 mm, and may have an inner diameter (ID) of about 0.35 mm.

FIG. 5C is a longitudinal cross-sectional view depicting the central portion (512) and the ends (514) and FIG. 5D is an end view of the FDM (510) where only one end (514) can be seen. In some variations, the central portion (512) of the FDM may comprise nitinol, while the ends (514) may comprise a bioabsorbable material such as 75:25 PGLA or any of the other bioabsorbable materials described above. An implant with FDMs having bioabsorbable ends may change the spacing between anchors (and therefore, the flexibility of the implant) over time. For example, upon initial implantation and implant cinching, the FDM may ensure that the distance between two anchors is no less than its total length $L_T$ (where $L_T = L_{non\text{-}bioabsorbable} + L_{bioabsorbable}$). Over time, as the bioabsorbable portions dissolve, the total length of the FDM may become shorter as the bioabsorbable end portions or lengths dissolve ($L_T$ at implantation time $t_0$ is greater than $L_T$ at a later time $t_0+\Delta t$ as $L_{bioabsorbable}$ decreases). This may allow the anchors and FDMs more flexibility to move closer together (i.e., closer than $L_T$ at implantation time $t_0$) as the heart beats, facilitating myocardial contraction. The length of the non-bioabsorbable portion $L_{non\text{-}bioabsorbable}$ may be the minimum distance desirable between two anchors. The proportion of the length of the FDM that is made of a bioabsorbable material may be selected or tuned based on the desired amount of movement (e.g., contraction) of the cardiac tissue or walls after implantation. That is, the length of the bioabsorbable portion $L_{bioabsorbable}$ may correspond with the desired reduction in distance, as the heart beats, between two anchors after the bioabsorbable portion has fully dissolved. For example, the proportion or percentage of the total length $L_T$ of the FDM that is comprised by the bioabsorbable portions or lengths $L_{bioabsorbable}$ (which may be, for example, the cumulative length of both end portions) may be from about 10% to about 90%, e.g., about 25%, about 30%, about 40%, about 50%, about 60%, about 75%, about 85%, about 90%, etc. The FDM (510) may have a total length $L_T$ from about 3 mm to about 10 mm, may have an outer diameter (OD) of about 2 mm, and may have an inner diameter (ID) of about 0.35 mm.

FIGS. 5E-5F depict one variation of a FDM (520) comprising a nitinol tube (522) having a lumen (521) therethrough, and a PET or UHMW polymer sleeve (524) located within the lumen (521). Alternatively, an inner surface of the lumen (521) may be coated with PET or a UHMW polymer. The PET or UHMW sleeve or coating (524) may provide a surface with a reduced coefficient of friction so that a tether may be passed through the lumen (521). The sleeve or coating (524) may have a thickness from about 0.7 mm to about 0.9 mm, e.g., about 0.825 mm. FIG. 5E is a longitudinal cross-sectional view and FIG. 5F is an end view of the FDM (520). In some variations, the FDM (520) may comprise a tube (522) made of a bioabsorbable materials and a PET or UHMW polymer sleeve within the lumen. The bioabsorbable material may be 75:25 PGLA or any of the other bioabsorbable materials described above. The FDM (520) may have a length (L) from about 3 mm to about 10 mm, may have an outer diameter (OD) of about 2 mm, may have an inner diameter (ID) of about 0.35 mm, and the outer diameter of the bioabsorbable portion ($OD_{bioabsorbable}$) may be about 1.25 mm.

Figure 5H:
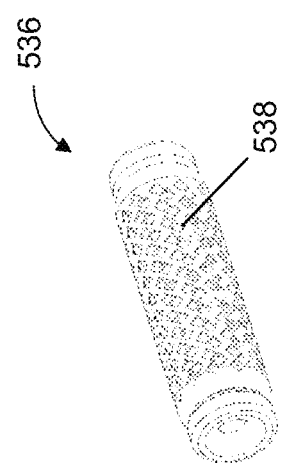
FIGS. 5G and 5H are perspective views of additional variations of FDMs.
Figure 5G:
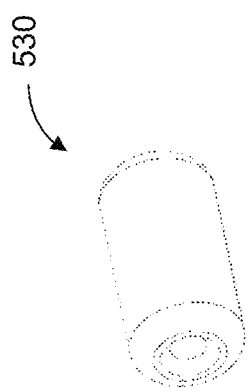

FIG. 5G depicts another variation of a FDM (530) comprising a tubular body made of a single material (e.g., biodegradable or non-biodegradable). FIG. 5H depicts another variation of a FDM (536) comprising a tubular body with external surface textures (538). Surface textures (538) may help encourage tissue in-growth and/or promote engagement between the implant and cardiac tissue.

Implant Assembly

Figure 6A:
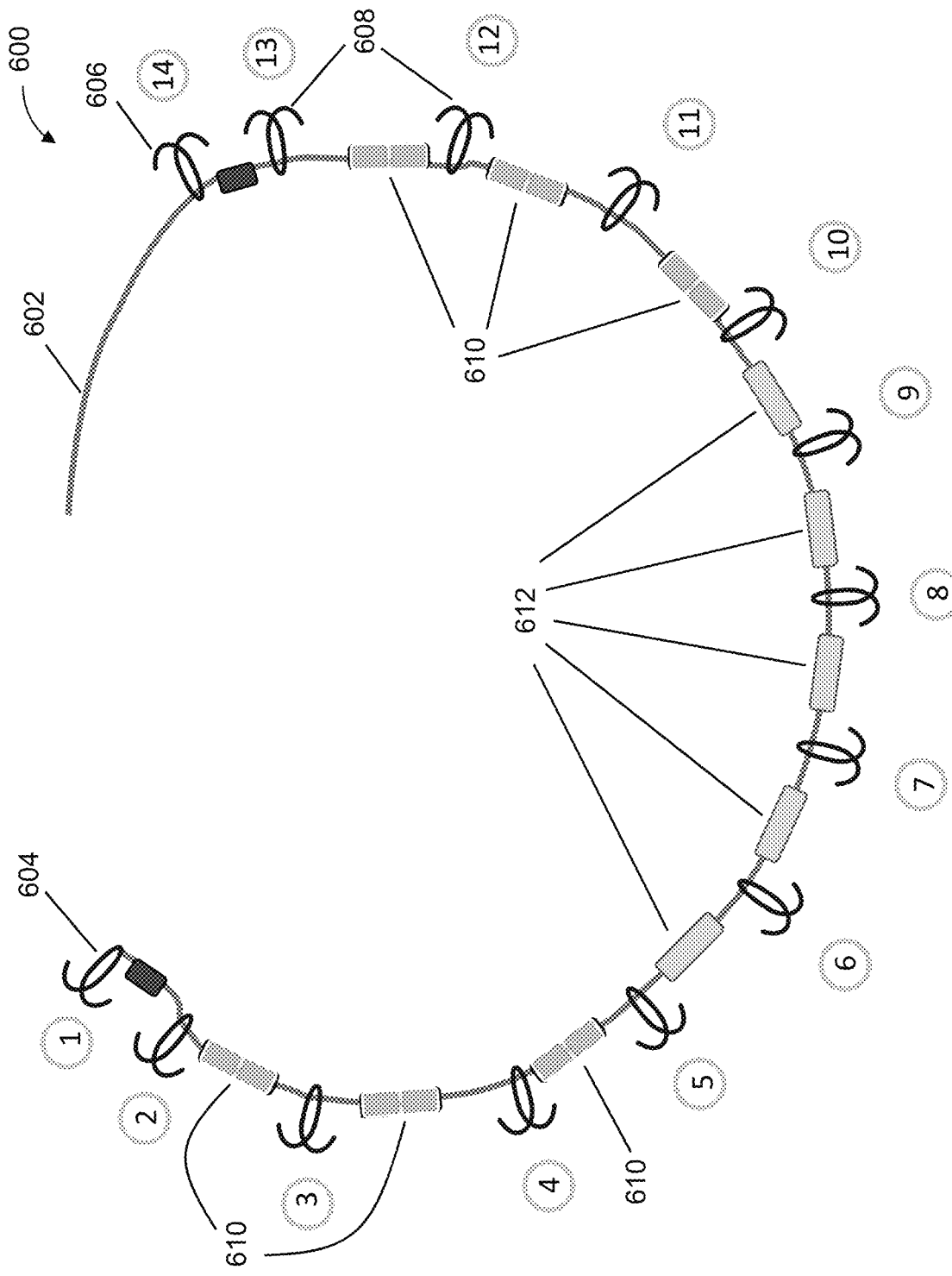
FIG. 6A is a schematic depiction of one variation of an implant.

FIG. 6A depicts one variation of an implant (600) comprising a tether (602), a plurality of tissue anchors (e.g., 14 tissue anchors) coupled to the tether (602) and a plurality of FDMs (e.g., 13 FDMs) coupled to the tether (602) between the anchors. The plurality of anchors may comprise a distal-most terminal anchor (604), a proximal-most terminal anchor (606), and a plurality of intermediate anchors (608) located between them. The distal-most terminal anchor and/or the proximal-most terminal anchor may be fixedly attached to the tether. For example, the tether may be fixedly attached (e.g., knotted, adhered, welded, etc.) to the distal-most terminal anchor while the proximal-most terminal anchor and the intermediate anchors may be slidably coupled the tether. After the implant is cinched, the tension in the tether may be retained by securing a lock device (not shown) to the tether proximal to the proximal-most terminal anchor. The FDMs (610) at the implant ends and/or along an end segment of the implant (e.g., between anchors 1-5 and 10-14) may be made of a non-bioabsorbable material such as nitinol while the FDMs (612) in a middle or intermediate segment of the implant (e.g., between anchors 5-10) may entirely bioabsorbable. For example, the FDMs (612) may be made of a bioabsorbable material such as 75:25 PLGA. Optionally, the FDMs (612) and/or FDMs (610) may comprise a drug-eluting material. The FDMs between the anchors of any of the implants described herein may have the same or may have varying lengths. For example, the FDMs between the terminal anchors and the next-to-terminal anchors (e.g., between the distal-most terminal anchor and the next-to-distal-most anchor, and/or between the proximal-most terminal anchor and a next-to-proximal-most anchor) may be shorter than the FDMs between the intermediate anchors (e.g., the anchors in a central region of the implant). In some variations, the shorter, terminal FDMs may not comprise polyester covers while the longer, intermediate FDMs may comprise polyester covers.

Figure 6B:
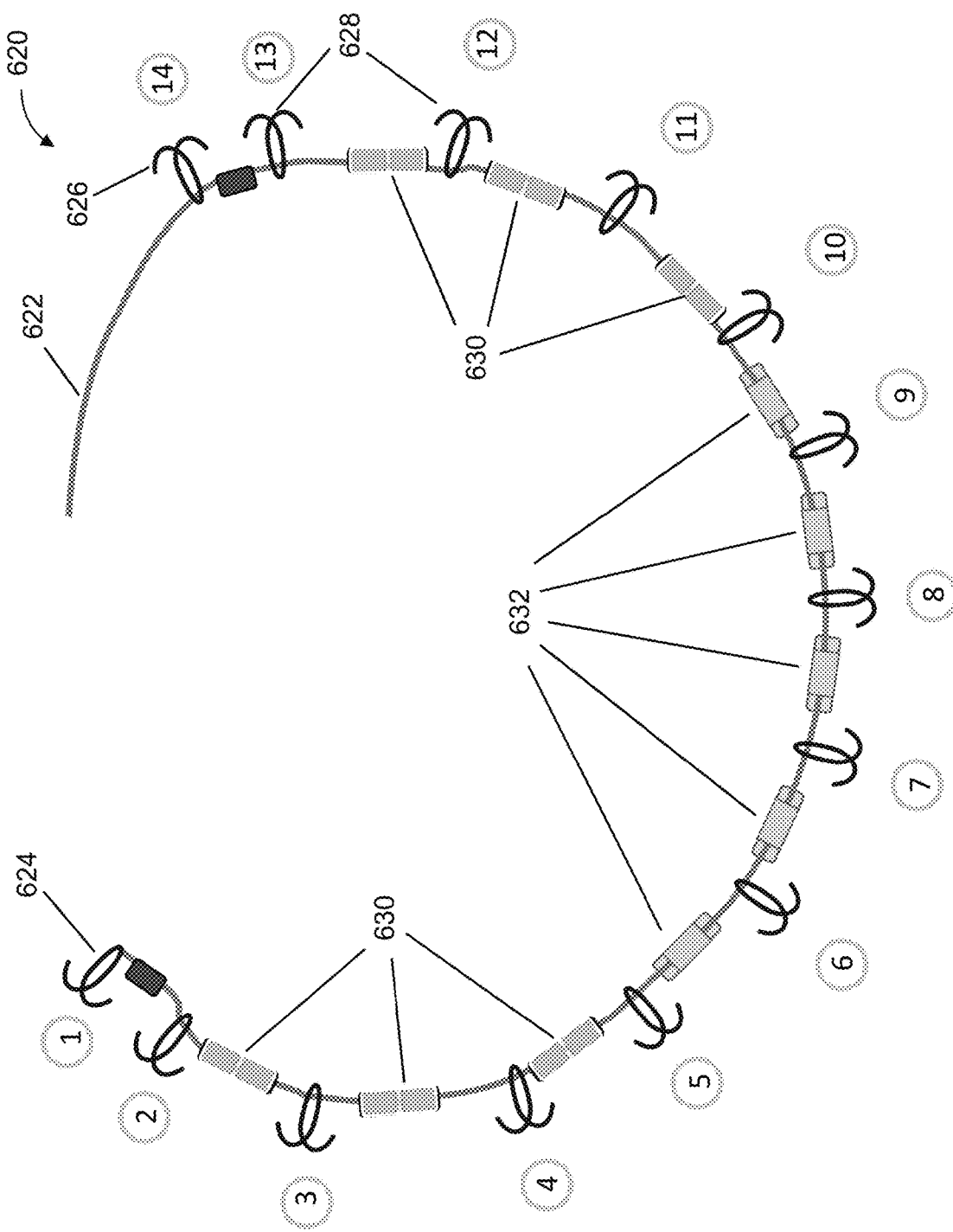
FIG. 6B is a schematic depiction of one variation of an implant.

FIG. 6B depicts one variation of an implant (620) comprising a tether (622), a plurality of tissue anchors (e.g., 14 tissue anchors) coupled to the tether (622) and a plurality of FDMs (e.g., 13 FDMs) coupled to the tether (622) between the anchors. The plurality of anchors may comprise a distal-most terminal anchor (624), a proximal-most terminal anchor (626), and a plurality of intermediate anchors (628) located between them. The distal-most terminal anchor and/or the proximal-most terminal anchor may be fixedly attached to the tether. For example, the tether may be fixedly attached (e.g., knotted, adhered, welded, etc.) to the distal-most terminal anchor while the proximal-most terminal anchor and the intermediate anchors may be slidably coupled the tether. After the implant is cinched, the tension in the tether may be retained by securing a lock device (not shown) to the tether proximal to the proximal-most terminal anchor. The FDMs (630) at the implant ends or along an end segment of the implant (e.g., between anchors 1-5 and 10-14) may be made of a non-bioabsorbable material such as nitinol while the FDMs (632) in a middle or intermediate segment of the implant (e.g., between anchors 5-10) may comprise a non-bioabsorbable central portion or length and bioabsorbable end portions or lengths. For example, the FDMs (632) may be similar to the FDM described and depicted in FIGS. 5C-5D. The non-bioabsorbable central portion or length may be made of a metal alloy such as nitinol and the bioabsorbable end portions or lengths may be made of a bioabsorbable material such as 75:25 PLGA. Optionally, the FDMs (632) and/or FDMs (630) may comprise a drug-eluting material.

Figure 6C:
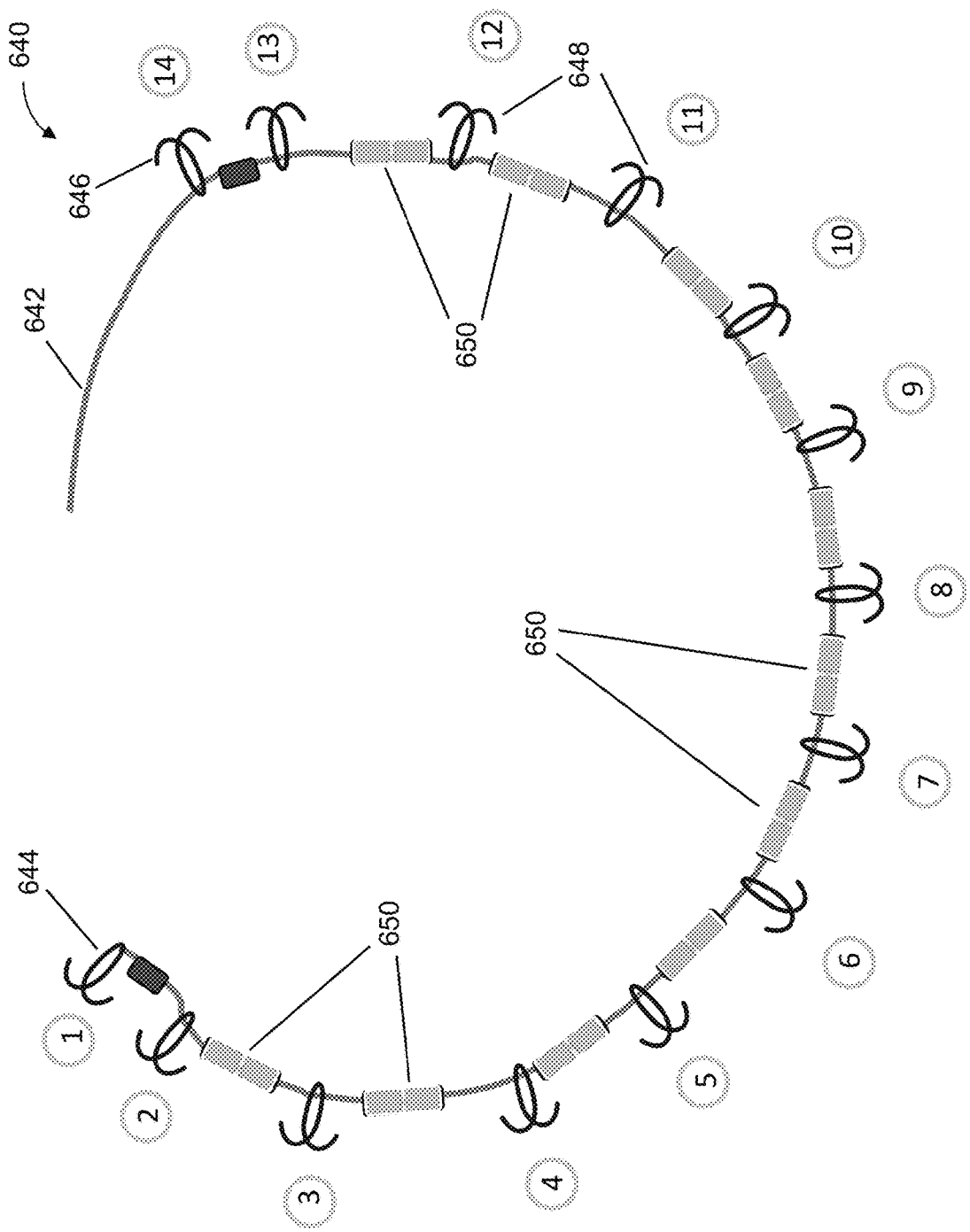
FIG. 6C is a schematic depiction of one variation of an implant.
Figure 6D:
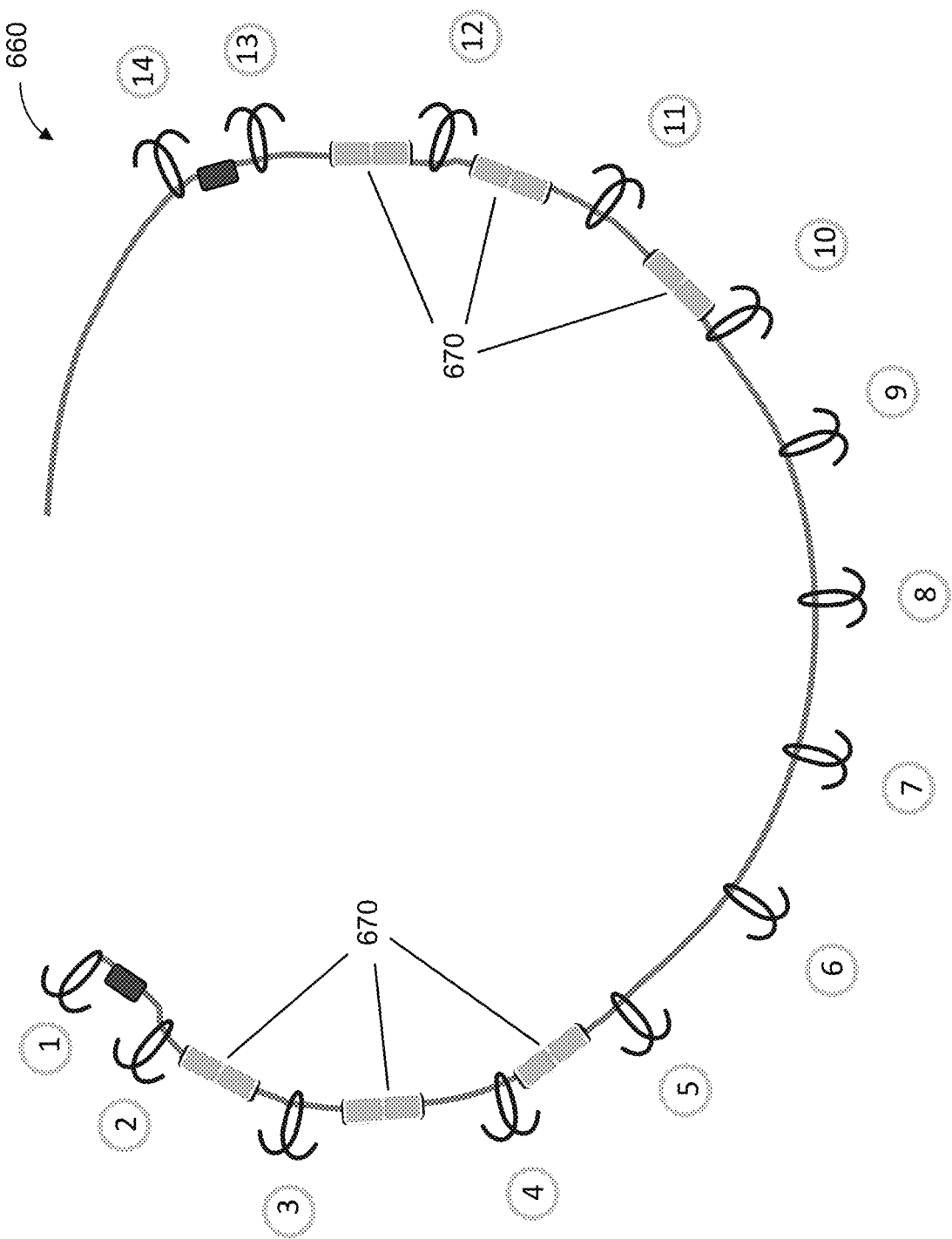
FIG. 6D is a schematic depiction of another variation of an implant.

FIG. 6C depicts one variation of an implant (640) comprising a tether (642), a plurality of tissue anchors (e.g., 14 tissue anchors) coupled to the tether (642) and a plurality of FDMs (e.g., 13 FDMs) coupled to the tether (642) between the anchors. The plurality of anchors may comprise a distal-most terminal anchor (644), a proximal-most terminal anchor (646), and a plurality of intermediate anchors (648) located between them. The distal-most terminal anchor and/or the proximal-most terminal anchor may be fixedly attached to the tether. For example, the tether may be fixedly attached (e.g., knotted, adhered, welded, etc.) to the distal-most terminal anchor while the proximal-most terminal anchor and the intermediate anchors may be slidably coupled the tether. After the implant is cinched, the tension in the tether may be retained by securing a lock device (not shown) to the tether proximal to the proximal-most terminal anchor. The FDMs (650) between all of the anchors (anchors 1-14) may be the same type of FDM. For example, the FDMs (650) may be entirely bioabsorbable (e.g., similar to the FDMs of FIGS. 5A-5B), may be partially bioabsorbable (e.g., similar to the FDMs of FIGS. 5C-5D), or may not comprise any bioabsorbable components at all (e.g., made entirely of a non-bioabsorbable material such as nitinol). The fully or partially bioabsorbable FDMs may be made of a bioabsorbable material such as 75:25 PLGA. Optionally, the FDMs (650) may comprise a drug-eluting material. Alternatively, as depicted in FIG. 6D, some implants (660) may comprise FDMs (670) located only at the implant ends and/or along an end segment of the implant (e.g., between anchors 1-5 and 10-14). The FDMs (670) may be any one or combination of the FDMs described above (e.g., any one or more of the FDMs described and depicted in FIGS. 5A-5H).

There may not be any FDMs located between the intermediate anchors (e.g., between anchors 5-10).

While the FDMs depicted in FIGS. 6A-6D are all the same length and may promote symmetric or equal tissue tightening along the entire length of the implant, it should be understood that the FDMs of an implant may differ from each other so that the tissue tightening along the implant is asymmetric, with local regions of increased or reduced tissue tightening. In some variations, the lengths of the FDMs in an implant may be varied to customize the magnitude of LV wall reduction in local areas, depending upon the patient's history. For cardiac regions where greater tissue tightening may be desired (e.g., a greater volume reduction in a localized portion of the ventricle or heart chamber, a greater reduction in a circumference or partial arc length of a valve orifice), shorter FDMs may be used. For example, if greater tightening is desired along the P2 portion of a posterior leaf of a mitral valve (or the P1 region, P1 and P3 regions, etc.), shorter FDMs, or no FDMs, may be used between the anchors that are implanted in that region. Alternatively, longer FDMs may be located along the portion of the implant that tracks along regions where less tissue tightening is desired. Longer FDMs may help to keep the anchors implanted in those regions further apart from each other so that the tissue is not drawn closely together when the implant is cinched. For example, in a patient with ischemic cardiomyopathy secondary to posterior wall MI, it may be desirable to emphasize wall reduction in the region of the posterior wall under P3 of the mitral valve. This can be done with an implant comprising FDMs of shorter length in the portion of the implant that is attached to the posterior wall under P3 of the mitral valve, which may help to produce greater tissue tightening and wall reduction. Other portions of the implant may have longer FDMs for less tissue tightening. Kits can be provided for commonly occurring histories such as MI induced cardiomyopathy, or to address localized wall distension identified during pre-procedure planning.

Figure 7B:
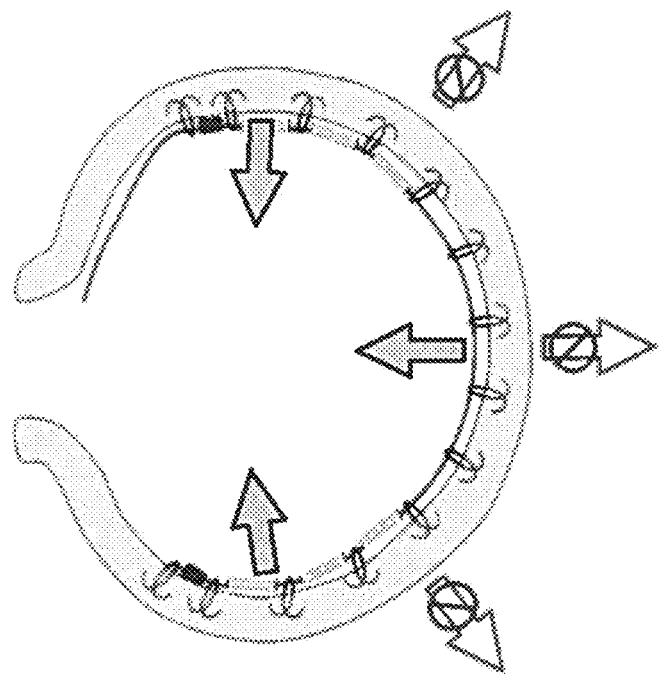
FIGS. 7A and 7B are schematic depictions of one variation of an implant with FDMs, in the uncinched and cinched conditions, respectively.
Figure 7A:
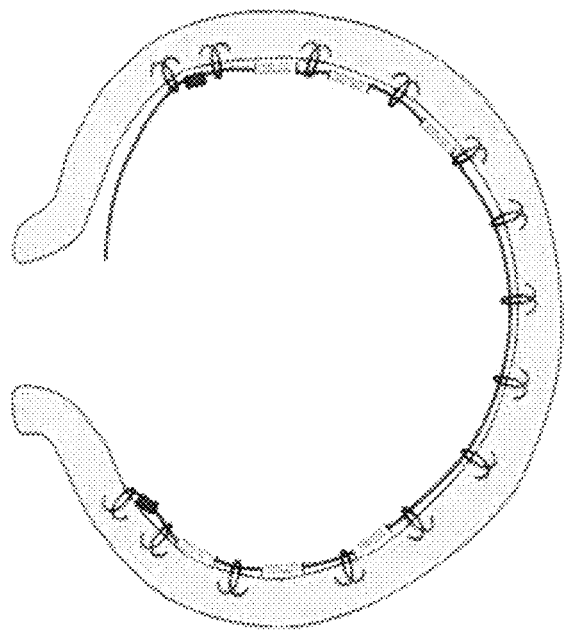

The implants described above and depicted in FIGS. 6A-6D may allow for differing ranges of motion for beating heart tissue, and depending on the disease state of a patient's heart, a clinician may select or recommend different implants to provide a desired tissue tightening profile. FIGS. 7A-7B depict the implant of FIG. 6D deployed into ventricular wall tissue in a subvalvular space of the left ventricle in an uncinched configuration and a cinched configuration, respectively. In this implant, FDMs are located between the anchors along the end segments of the implant. The FDMs may couple several anchors together at each end of the implant, while the balance of intermediate anchors remain uncoupled. The cinched implant, as depicted in FIG. 7B, cannot distend beyond what the implant allows during diastole, but can contract to end systole unimpeded.

Figure 8B:
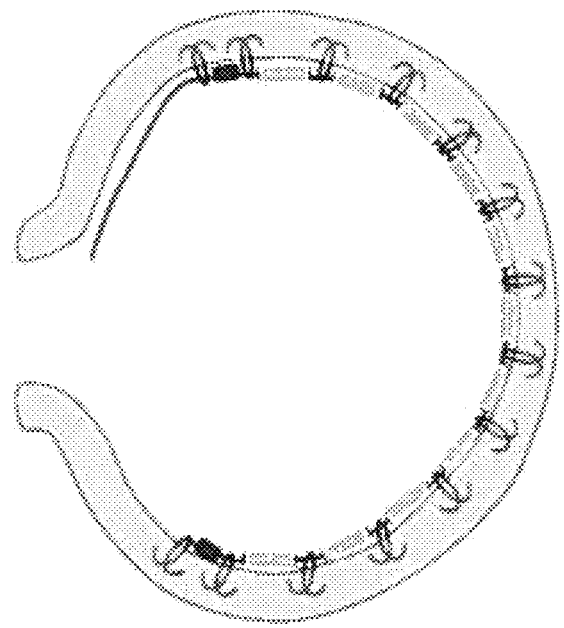
FIGS. 8A and 8B are schematic depictions of one variation of an implant with FDMs, in the uncinched and cinched conditions, respectively.
Figure 8A:
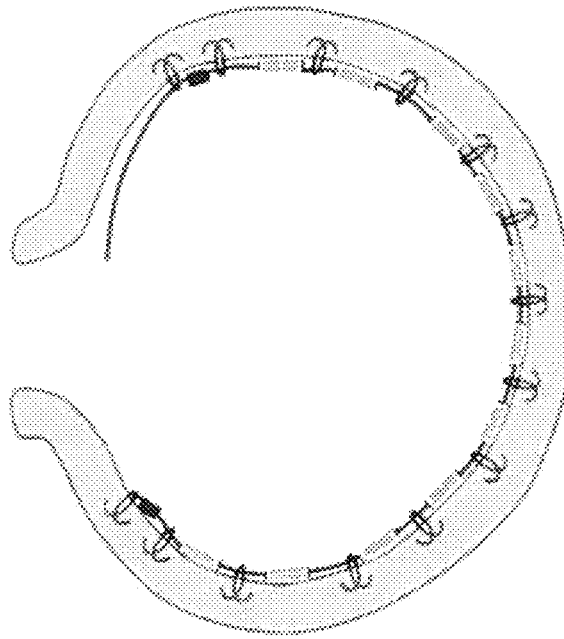

FIGS. 8A-8B depict the implant of FIG. 6C deployed into ventricular wall tissue in a subvalvular space of the left ventricle in an uncinched configuration and a cinched configuration, respectively. In this implant, FDMs are located between all of the anchors of the implant. This may help to improve the implant load carrying capacity in a subset of patients with friable myocardium. Including FDMs between each anchor may help to maintain a desired level of tissue tightening along the LV wall. An implant comprising FDMs between each of the plurality of anchors may facilitate a sustained reduction in LV diameter in the presence of general or local variations in wall strength due to trabeculations (non-compacted myocardium) or fibrotic tissue secondary to prior MI, or friable myocardium due to viral infections, alcoholism or other causes of dilated cardiomyopathy, that may otherwise compromise load capacity at the anchor-tissue interface. The implant of FIG. 6C and FIGS. 8A-8B may allow the implant to be cinched to a hard stop—the point at which all anchors are coupled together (FIG. 8B). This configuration is may provide a desirable margin of safety in that it prevents over-cinching the LV wall during the procedure. Once the hard stop has been reached, additional tension on the tether induces no additional implant cinching and no further strain in the myocardial tissue. It is also simpler to cinch in that no measurements are required during the cinching process to determine the appropriate stopping point. To further understand the effect of the different implants described above, it may be helpful to consider LV wall motion under several conditions, as described below.

Figure 9:
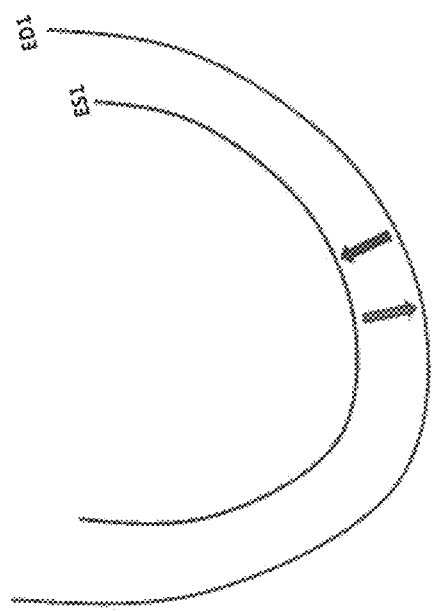
FIG. 9 is a schematic view of the motion of the LV free wall from diastole to systole.

FIG. 9 is a schematic depiction of the LV free wall of a patient with MR and HF, in which the free wall moves from end diastole (ED1) to end systole (ES1) and back again. In such a patient, ED1 is enlarged compared to the normal population (baseline), inducing reduced wall thickness, increased wall stress, and compromised myocyte contractility. This may lead to an end systole (ES1) that is also larger compared to baseline, and a distance between ED1 and ES1 that is significantly reduced compared to the baseline.

Figure 10:
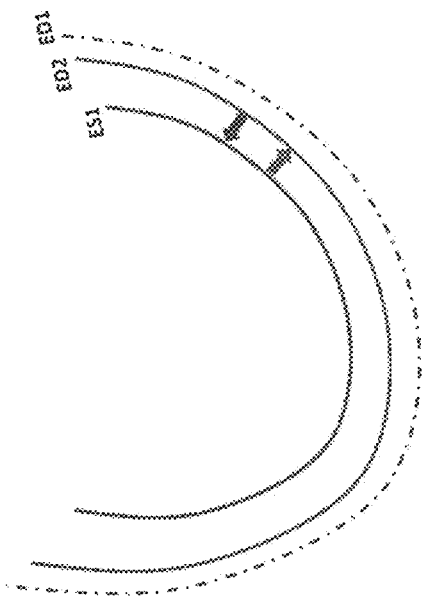
FIG. 10 is a schematic view of the LV free wall with an implant containing FDM anchor blocks.
Figure 11:
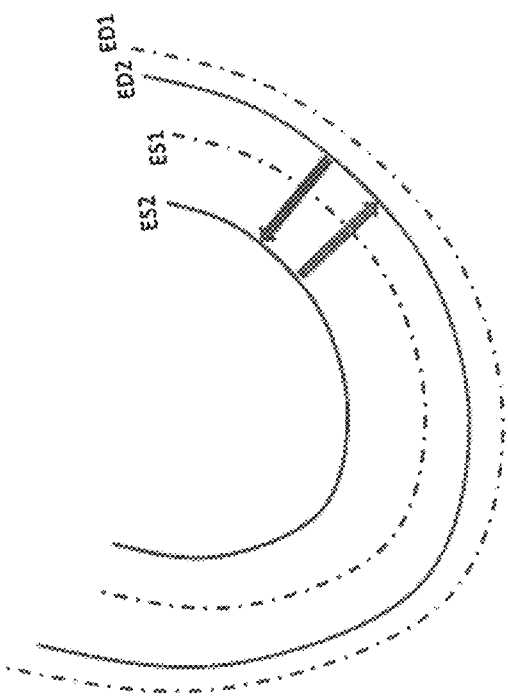
FIG. 11 is a schematic view of the LV free wall with improved LV function.

FIG. 10 is a schematic depiction of heart wall movement in the patient described above who has received an implant with FDM blocks at its ends (e.g., such as the FIG. 6D implant) in the LV wall of FIG. 9. The implant may be cinched to ED2, which is located between ED1 and ES1. During diastole the LV cannot expand beyond ED2 due to the non-distensible implant tether, which improves LV function by reducing wall stress. Since the intermediate anchors can move freely, during systole the LV can contract freely to at least ES1. Over time, reverse remodeling and improved myocyte contractility could lead to an improved (smaller) end systole ES2 that more closely approximates baseline, as shown in FIG. 11, which may indicate improved LV function.

Figure 12:
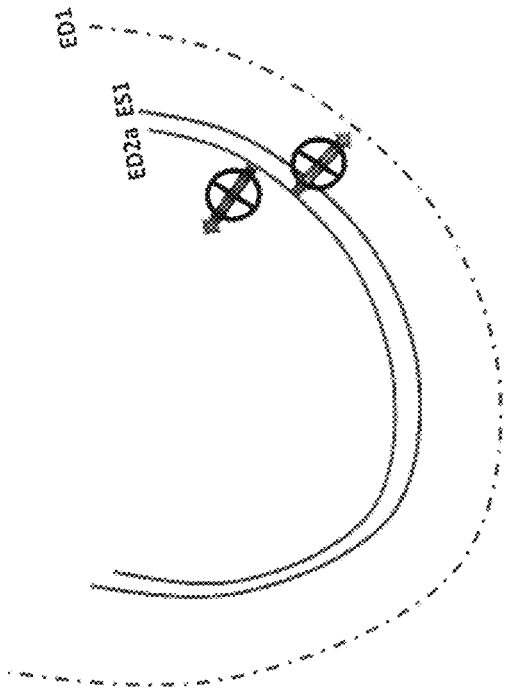
FIG. 12 is a schematic view of the LV free wall cinched past end systole.
Figure 13:
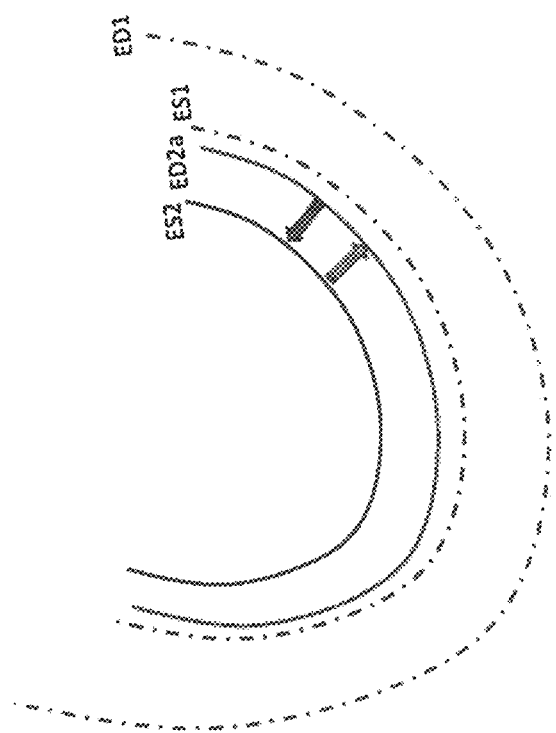
FIG. 13 is a schematic view of the LV free wall cinched past end systole, showing improved LV function.

Alternatively, an implant comprising FDM blocks, may be cinched to ED2a, which may be coincident to or smaller than ES1, as shown in FIG. 12. In this condition, the LV may not move in either direction acutely: the implant may prevent expansion of the LV wall past ED2a and the LV wall may not contract further than ES1. Initially, cardiac function may be reduced. In this condition as well, however, improved contractility over time could lead to improved (smaller) end systole, ES2 (FIG. 13) that approximates baseline, which together with a reduced ED2a may indicate improved LV function. While the implants of FIGS. 6C-6D, 7A-7B, 8A-8B may provide such improvements to LV function, the implant of FIGS. 6C and 8A-8B having FDMs located between every anchor may react less force at the anchor-tissue interface than the implant for FIGS. 6D and 7A-7B having FDMs located only between anchors in an end portion or length of the implant. For patients having friable myocardium, a clinician may recommend the implant of FIG. 6C over the implant of FIG. 6D.

Figure 14:
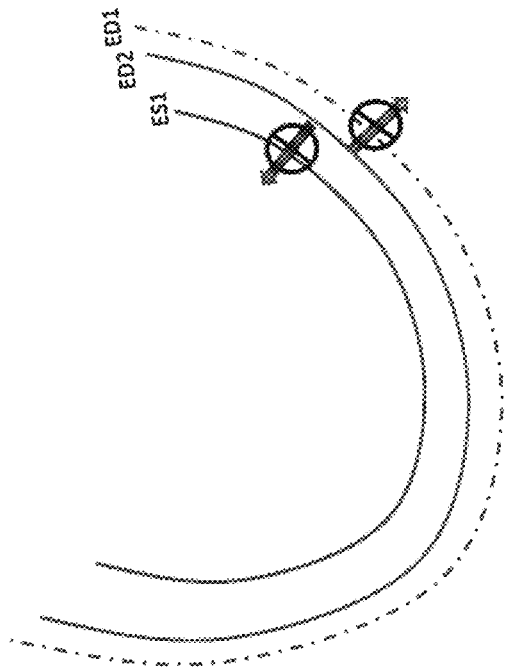
FIG. 14 is a schematic view of the LV free wall with an implant cinched to a hard stop.

However, for the implant of FIG. 6C (as deployed in FIGS. 8A-8B), when cinched to its hard stop as shown in FIG. 8B, the implant may become incompressible. That is, the implant can bend, but its perimeter cannot be further reduced. Not only does this implant prevent LV expansion during diastole, but at systole it may also limits the ability of the LV in the region of the implant to contract toward its end systolic dimension. Consider an LV with end diastole at ED1 and end systole at ES1 as shown in FIG. 14, and an implant cinched to its hard stop such that end diastole moves to ED2, located between ED1 and ES1. As with other implant configurations, in diastole the LV cannot expand beyond ED2. But during systole the hard stop may prevent further contraction toward ES1, restricting local wall motion, and effectively eliminating this region of the LV from contributing to cardiac output.

The implant of FIG. 6C (as deployed in FIGS. 8A-8B), when cinched to its hard stop, may not be compressible, but may be flexed. Acutely, or over time, the LV in the regions near the implant ends (under P3 and P1) may contract at the expense of the region in the middle (under P2), which may expand to accommodate the P3, P1 contraction. This motion is depicted as line ES2 in FIG. 15. Clinically, the result may present as a decrease in the commissural (c/c) dimension but an increased anterior/posterior (a/p) dimension. The opposite motion may also present clinically—a decrease in the a/p dimension and consequent increase in the c/c dimension.

Figure 15:
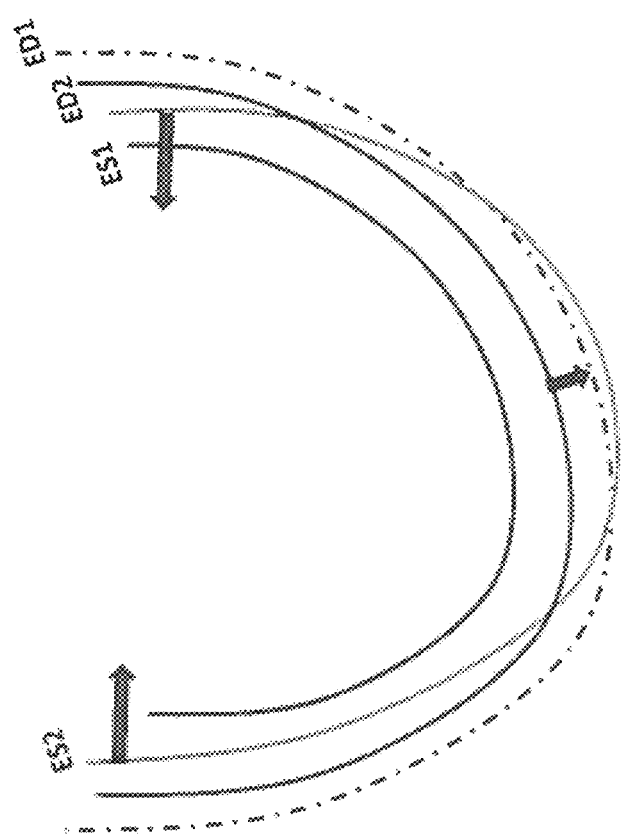
FIG. 15 is a schematic view of the motion of the LV free wall in the presence of an implant cinched to a hard stop.

To overcome the possibly detrimental impact on LV function in the region of the implant shown in FIG. 15, yet maintain the advantages of the implant of FIG. 6C over the implant of FIG. 6D, the net cinch at the end of the procedure may allow contraction toward end systole. An implant that addresses these challenges may have small gaps between anchors and FDMs in the intermediate anchor locations (e.g., in a central region of the implant). For example, an implant with 14 anchors total, including 5 anchors in the blocks at each end, there may be 5 FDMs with gaps to the anchors, as depicted in FIG. 16A. The detailed view of FIG. 16B shows the gap locations. In this variation, there may be gaps of about 1.5 mm to about 3.5 mm (e.g., about 2.5 mm, about 3 mm) between the intermediate FDMs (with the intermediate anchors disposed in the gaps between the FDMs), and little or no gaps between the FDMs and the anchors on the terminal regions of the implant (e.g., the distal region, the proximal region). A pre-selected amount of slack may be provided to the implant by cinching the implant to its hard stop configuration and securing a lock member a pre-selected tether length away from the proximal-most anchor. In some variations, the pre-selected tether length may be from about 5 mm to about 15 mm, e.g., about 9.5 mm, about 10 mm. Introducing too much slack to the implant (e.g., providing a pre-selected tether length to the hard stop configuration greater than 20 mm) may not provide the desired reduction in cardiac dimensions. Without wishing to be bound by theory, the reduced LV size depicted in FIG. 16A, along with small gaps between anchors and FDMs, may help facilitate reverse remodeling by several mechanisms. First, the LV diameter itself may be reduced. For a given pressure in the system, the smaller surface area places a lower total load on the wall. In addition, wall stress is reduced by the law of Laplace, which may account for both a diameter decrease as well as the corresponding LV wall thickening. In addition to these mechanisms, the reduced wall size and stress potentially can improve myocyte contractility. Sarcomere isometric muscle force is a function of sarcomere length. Muscle force may be maximized in the cardiac sarcomere at 2.0-2.2 µm, and it may drop off to less than 20% of maximum below about 1.8 µm and above about 2.4 µm. In the HF ventricle, cardiac sarcomeres can be elongated well beyond the length that produces the most efficient contraction (2.0-2.2 µm). In later stages of HF, the myocytes can be elongated to the point that myosin and actin proteins fail to bond or produce any contractile force. Cinching the LV wall to a smaller diameter potentially may facilitate improved myosin/actin overlap, bonding, and thus contraction.

Figure 17A:
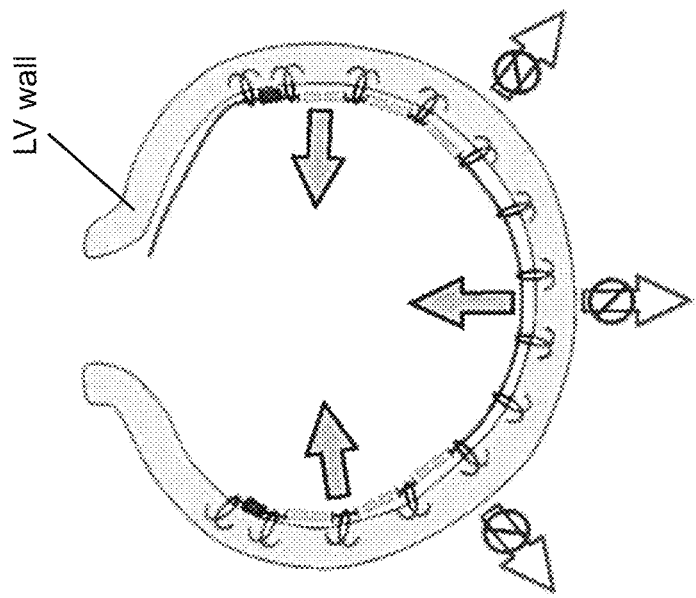
FIGS. 17A and 17B depict a cinched implant with bio-absorbable FDMs at the intermediate locations, shown acutely and at follow up, respectively.
Figure 17B:
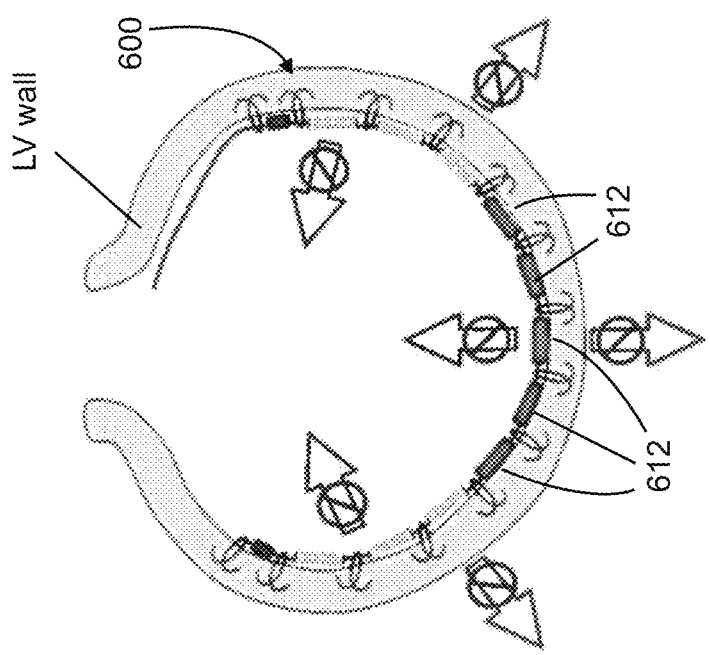

An implant with one or more bioabsorbable FDMs between the anchors may help facilitate contraction toward end systole over time. FIG. 17A depicts the implant of FIG. 6A, having a plurality of bioabsorbable FDMs between the intermediate anchors, deployed and implanted into ventricular wall tissue in a subvalvular space of the left ventricle. Upon initial implantation, the implant (600) may greatly limit LV wall motion as depicted in FIG. 17A, but as the intermediate FDMs are bioabsorbed, and completely dissolve, as depicted in FIG. 17B, the LV wall becomes free to contract more fully to end systole. As described previously, the bioabsorbable FDMs may take from about 1 month to about 4 months, e.g., about 3 months, about 90 days to dissolve. In some variations, the bioabsorbable FDMs may be made of a material that fully dissolves after the non-bioabsorbable FDMs are incorporated into ventricular wall tissue. For example, for implants where the non-bioabsorbable FDMs take about 3 months or 90 days to be incorporated into cardiac tissue, the material of the bioabsorbable FDMs may be selected such that they fully dissolve in about 4 months. In some variations, the bioabsorbable FDMs may be made of a material that loses its mechanical properties (i.e., becomes soft or amorphous) without fully dissolving after the non-bioabsorbable FDMs are incorporated into ventricular wall tissue.

Figure 18B:
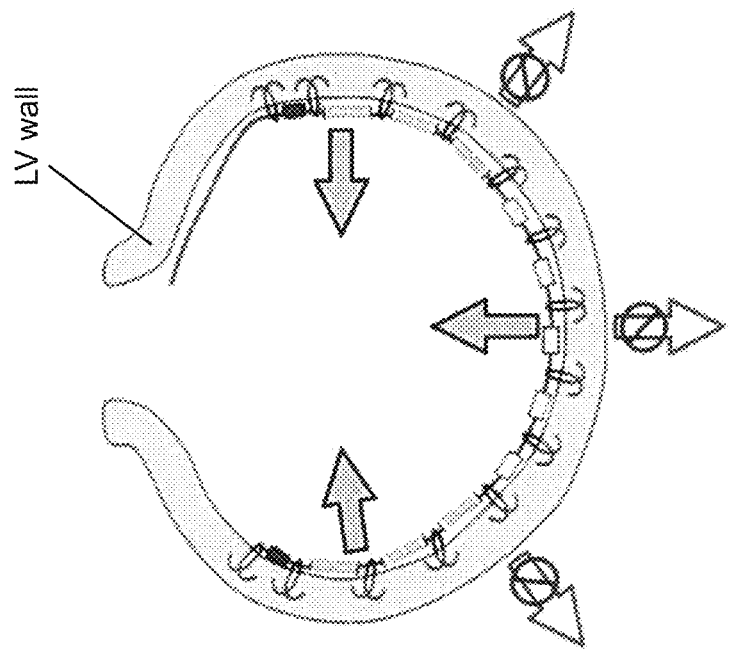
FIGS. 18A and 18B depict a cinched implant with partially bio-absorbable FDMs at the intermediate locations, shown acutely and at follow up, respectively.
Figure 18A:
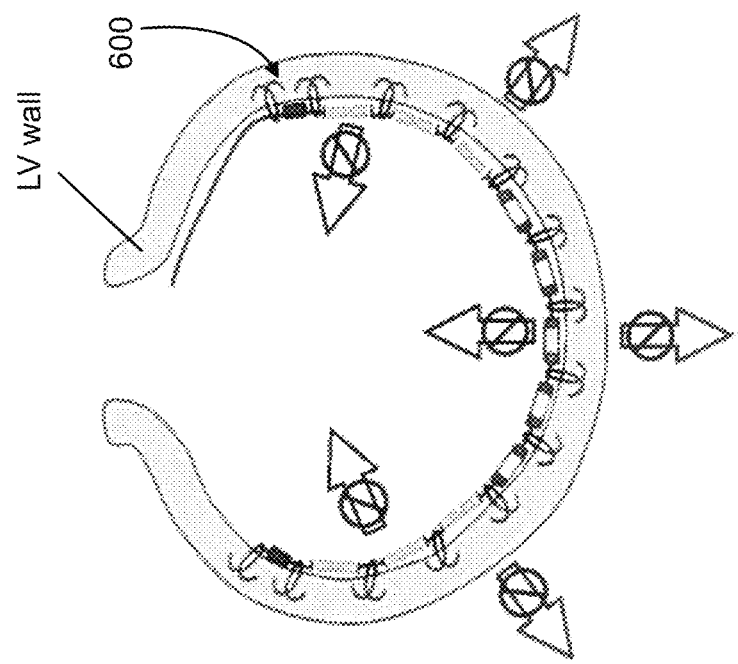

FIG. 18A depicts the implant of FIG. 6B, having a plurality of partially bioabsorbable FDMs between the intermediate anchors, deployed and implanted into ventricular wall tissue in a subvalvular space of the left ventricle. As described above, the FDMs may have a non-bioabsorbable central portion or segment and bioabsorbable end portions or segments. Upon initial implantation, the implant (620) may greatly limit LV wall motion as depicted in FIG. 18A, but as the bioabsorbable portion of the FDMs are bioabsorbed, their total length may be reduced, as depicted in FIG. 18B, the LV wall may become free to contract more fully to end systole. Because the bioabsorbable portion of the FDMs is only a sub-portion of the entire FDM, it may degrade more rapidly as compared to a fully bioabsorbable FDM. For example, the bioabsorbable portion of the FDMs may take from about 0.5 month to about 2 months, e.g., about 1.5 months, about 45 days, to dissolve. In some variations, the bioabsorbable portion of the FDMs may be made of a material that fully dissolves after the anchors incorporated into ventricular wall tissue. For example, for implants where the anchors take about 3 months or 90 days to be incorporated into cardiac tissue, the material of the bioabsorbable portion of the FDMs may be selected such that they fully dissolve in about 4 months.

Figure 19C:
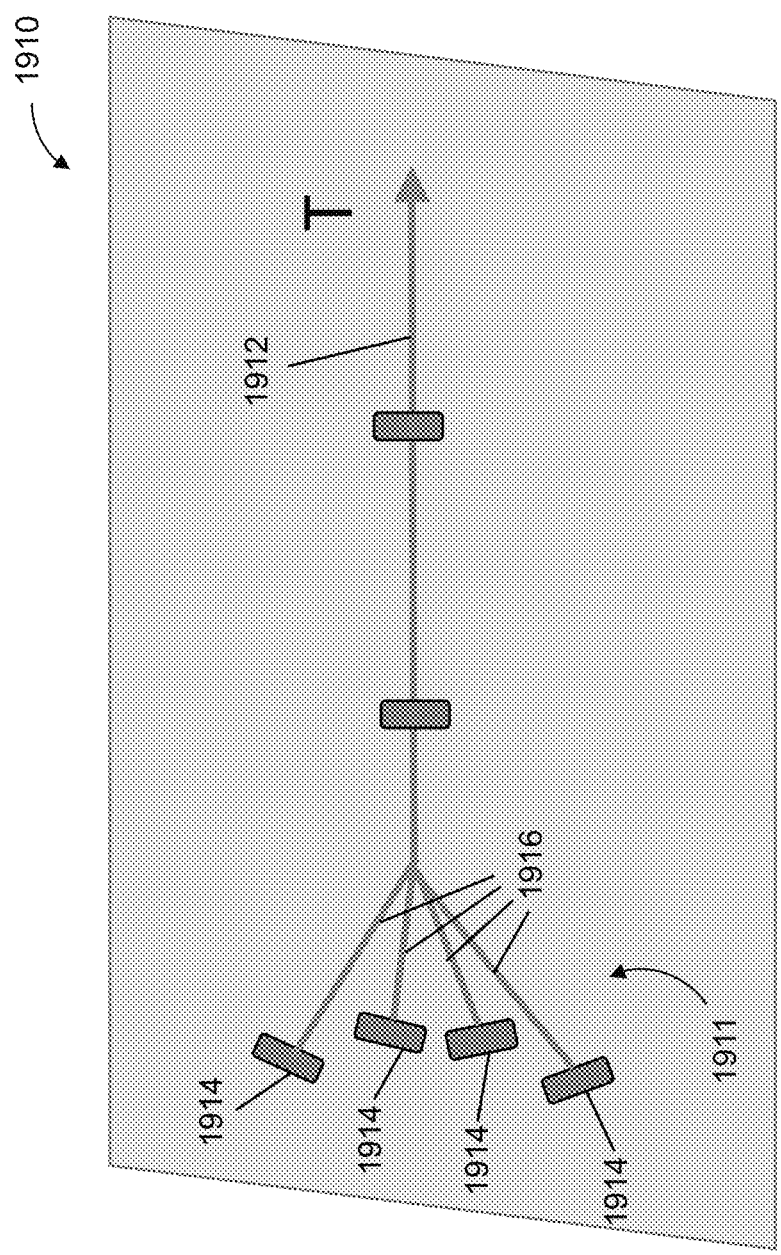
FIG. 19C depicts an implant with parallel, fixed end-anchors to distribute the load due to tension (T) in the tether.

Other implants that may be used to tighten cardiac tissue are depicted in FIGS. 19A-19F. FIGS. 19A-19B depict one variation of an implant (1900) comprising a tether (1902) or suture that is barbed along a distal segment, a flexible sleeve disposed over the barbed portion of the tether, and a plurality of anchors (1904) slidably disposed over the flexible sleeve. The flexible sleeve (not depicted) may comprise a thin-walled, flexible polymer over which the anchors may slide (i.e., the coefficient of friction of the sleeve may be less than the coefficient of friction of the barbed portion of the tether). In some variations, the distal-most end of the barbed portion of tether (1902) may comprise a crimp, knot, or other securing mechanism (1906) that prevents the tether from being pulled through the anchors. In some variations, the distal-most end of the tether may be fixedly attached to the distal-most anchor. The implant may be delivered to the cardiac tissue and the anchors deployed into and attached to the tissue with the flexible sleeve disposed over the barbed tether. Once the implant has been cinched to a known or pre-determined endpoint (e.g., implant hard stop), the sleeve can be removed to expose the barbs which may then act to fix the anchors in place on the tether, coupling them together to share the end-anchor load. A detailed view of the barbed suture interface with the anchor after the polymer is removed is shown in FIG. 19B. This may couple several anchors together at both implant ends, distributing higher end-anchor tangential load among several neighboring anchors that experience only the lower radial load.

FIG. 19C depicts another variation of an implant (1910) comprising a plurality of anchors (1914) fixedly coupled to tether segments (1916) at a distal end region (1911) of the implant (1910). One end of the tether segments (1916) may be fixedly attached to the anchors (1914) and the other end of the tether segments may all be attached to a main tether or cable (1912). In this configuration, the anchors (1914) may distribute the end load over multiple anchor points (e.g., the end load or force may be distributed in parallel at the implant end region over a larger tissue area over multiple anchors, instead of being concentrated over a smaller tissue area around a single anchor). The tether segments (1916) may be attached to the main tether (1912) by being knotted, woven, welded, and/or brazed together, and/or may be attached using adhesives (e.g., epoxy), and the like.

FIGS. 19D-19F depict another variation of an implant (1920) comprising a tether (1922), a distal-end anchor (1924) (e.g., A1 anchor) fixedly coupled to the tether, and a plurality of intermediate anchors (1926) (e.g., A2, A3 anchors) slidably coupled to the tether. In this variation, the anchor (1925) that is immediately adjacent to the distal-end anchor (1924) may be closer to the distal-end anchor than it is to the adjacent intermediate anchor. The anchor (1925) may be slidably coupled to the tether, but when the implant (1920) is deployed to cardiac tissue, the anchor (1925) may be attached to tissue closer to the distal-end anchor (1924) than it is to the adjacent intermediate anchor (1926). Alternatively, both the distal-end anchor (1924) and the anchor (1925) adjacent to it may be fixedly attached to the tether (1922). As depicted in FIG. 19E, when a proximally directed force applied to the tether (1922), thereby applying a tension T to the implant, the distal-end anchor (1924) may be pulled toward the anchor (1924). FIG. 19F depicts another example where three distal anchors are located in relatively close proximity to each other such that tensioning the tether causes the anchors to contact each other and brace against the tension force T. In this manner, the forces reacted at the anchor-tissue interface may be distributed between at least the two distal-most anchors A1, A2 (FIG. 19E), or may be distributed between the three anchors A1, A2, A3 (FIG. 19F). The amount of tension that may be sustained by the implant without being pulled out from the tissue and/or causing further tissue damage may increase as the number of anchors that contact each other increases. For example, the tension force that may be sustained by the implant of FIGS. 19D and 19E may be about 0.2 lbf while the tension force that may be sustained by the implant of FIG. 19F may be about 0.5 lbf.

Offset Lock Member and Delivery Devices

Once the implant has been deployed/attached to cardiac tissue and cinched, a lock member may be secured to the tether to maintain the cinch and retain the tension applied to the tether. The lock member may be any suitable suture lock member, and may, in some variations, comprise a tube and a plug configured to fit within a lumen of the tube. The tube and/or plug may comprise one or more openings for the passage of the implant tether though the lumen. To deploy the lock, the plug may be pushed into the tube to clamp the tether between the walls of the lock plug and tube. The lock may be secured on the tether by friction fit, snap fit, screw fit, and/or any other suitable mechanism. A lock member may be deployed and secured over a tether using a lock deployment catheter. In some variations, a lock deployment catheter may comprise an elongate body with a longitudinal lumen that terminates at a distal opening, a lock member located at a lock member docking section in the lumen, and a push member within the longitudinal lumen. In some variations, the push member may be a push cable. After an implant is cinched to a desired state, the tether may be threaded through the lumen of the lock tube, the push member advanced distally to move the plug into the tube to secure the lock member over the tether. Once the lock member is secured over the tether, the lock member may be released from the docking section of the deployment catheter and may exit the longitudinal lumen of the elongate body through the distal opening. Alternatively, the lock member may exit the deployment catheter though a lock exit opening that may be located anywhere along the longitudinal lumen. A lock deployment catheter may also comprise a stop member within the longitudinal lumen to limit distal advancement of the push member.

In some variations, a lock deployment catheter may be configured to introduce a pre-selected amount of slack or reduction in tether tension when securing the lock member over the tether. In one variation, a lock deployment catheter may be configured to provide a pre-selected length of tether to an implant after the implant has been cinched to its hard stop configuration. For some implants, the pre-selected length of tether may be about 9.5 mm or about 10 mm, which may translate to an amount of slack such that the intermediate FDMs in a central region of the implant may be separated from each other (with an anchor between them) by a gap from about 2 mm to about 2.5 mm. A lock deployment catheter may secure the lock member at a pre-selected distance (i.e., a lock distance offset $d_{offset}$) away from the proximal-most terminal anchor so that a corresponding pre-selected amount of slack is provided to the implant. For example, if the lock is secured immediately adjacent to the proximal-most terminal anchor (i.e., $d_{offset}$ is about 0 mm away from the proximal-most terminal anchor), little if any slack is provided to the implant, and the separation gap between intermediate FDMs may be small or nearly zero. If the lock is secured on the tether at a proximal location offset from the proximal-most terminal anchor (e.g., $d_{offset}$ is from about 5 mm to about 15 mm away from the proximal-most terminal anchor, about 9.5 mm, about 10 mm, providing a corresponding length of tether), an amount of slack that corresponds to $d_{offset}$ may be provided to the implant, and the separation gap between intermediate FDMs may be from about 1.5 mm to about 3.5 mm (e.g., about 2 mm to about 2.5 mm).

Alternatively or additionally, a lock deployment catheter may secure the lock member at a pre-selected distance (i.e., a lock distance offset $d_{offset}$) away from the proximal-most terminal anchor so that a corresponding pre-selected amount of tension reduction is provided to the implant. For example, if the implant is cinched to have a peak tension $T_p$, the lock deployment catheter may secure the lock member at a pre-selected distance (i.e., a lock distance offset $d_{offset}$) away from the proximal-most terminal anchor so that a corresponding pre-selected amount of tension $T_s$ is released, such that the actual tension $T_a$ in the locked implant is $T_a = T_p \times T_s$. For example, if the lock is secured immediately adjacent to the proximal-most terminal anchor (i.e., $d_{offset}$ is about 0 mm away from the proximal-most terminal anchor), $T_a$ may approximate $T_p$. If the lock is secured on the tether at a proximal location offset from the proximal-most terminal anchor (i.e., $d_{offset}$ is more than about 1 mm away from the proximal-most terminal anchor), $T_a$ may be less than $T_p$. The magnitude of the offset (dx) may be pre-selected such that it corresponds to a pre-selected amount of tension reduction $T_s$.

In use, an implant (such as the implants of FIGS. 6A-6D) may be cinched to a hard stop, where further cinching of the implant will cause no further tissue tightening). This may help to maintain repeatability and precision of the procedure, since no measurements need to be taken in order to determine whether the implant has been cinched to its hard stop configuration. The distance (dx) in the lock deployment catheter may represent an offset length of implant tether, between the proximal end of the catheter and the distal end of the lock. Once the lock is secured on the tether and released, a known amount of cinch cable slack, corresponding to the length (dx), is released back into the implant. Over several cardiac cycles the slack may work its way along the implant to the intermediate anchors and/or FDMs, creating small gaps between FDMs and anchors in that region of the implant (as depicted in FIG. 16A). The higher load at the ends of the implant may cause the anchor blocks to maintain their solid height. The small gaps between the intermediate FDMs and intermediate anchors may allow further LV wall contraction toward end systole acutely and, as the heart remodels over time, facilitates LV wall contraction to correspondingly smaller end systolic dimensions. The upper bound on gap size may be limited by friable myocardium strength—if anchors pull through tissue at the FDMs, it may be desirable for the next intermediate anchor to couple to the FDM, increasing its load capacity, with a minimal amount of travel. The greater the travel required to couple the next anchor, the more cinch is lost in the implant. In some variations, a lock deployment catheter may be configured to have a distance (dx) such that the gaps between anchors (e.g., intermediate anchors, intermediate FDMs) may be from about 0.5 mm to about 4 mm (e.g., about 1 mm, about 2 mm, about 2.5 mm gap). Providing gaps between intermediate anchors and FDMs may facilitate LV wall motion during systole, while also facilitating the coupling of adjacent anchors via a FDM (e.g., to help distribute load forces over multiple anchors, to reduce the load force per individual anchor). A lock deployment catheter may have a fixed distance (dx), or may be configured to vary the distance (dx) in order to attain a different, pre-selected level of tether slack. For example, there can be a set of lock deployment catheters with different lengths of (dx) so that a particular lock deployment catheter may be selected in order to provide a pre-selected amount of slack for a patient and/or implant. Alternatively or additionally, a single lock deployment catheter may be configured such that the distance (dx) is adjustable by the user to set the gap width for a given patient and/or implant.

As described above, an implant may be cinched to a "hard stop" and when deploying the lock over the tether, the lock deployment catheter may secure the lock at a pre-selected offset $d_{offset}$ away from the proximal-most anchor in order to apply a pre-selected amount of slack to the implant. To apply a consistent and pre-selected amount of slack to a tether while applying the lock member, the lock member docking section (i.e., the location of the lock member within the lock deployment device when it is secured to the tether) may be set further away (proximally) from the distal opening of the elongate body. In other words, the docking section may be offset from the lock exit opening by a pre-selected offset (dx). In some variations, the docking section offset (dx) may be about the same as the lock distance offset $d_{offset}$, while in other variations, the lock distance offset $d_{offset}$ may be greater than the docking section offset (dx). For example, in addition to the docking section offset (dx), an additional offset may be introduced by the actual point of contact between the lock member and the tether (e.g., the point at which the lock is secured to the tether). Optionally, in variations where the lock exit opening is not positioned at the proximal-most terminal anchor, an additional offset may be introduced which may be the distance between the lock exit opening and the proximal-most terminal anchor. For example, if the lock exit opening is positioned $d_{cath}$ distance away from the proximal-most terminal anchor, the docking section offset is dx, and the lock member introduces an offset of $d_{lock}$, the total lock distance offset may be the sum of all of these offsets, i.e., $d_{offset}=dx+d_{cath}+d_{lock}$. In variations where the lock exit opening is positioned up against the proximal-most terminal anchor, $d_{offset}=dx+d_{lock}$. The locking mechanism of the lock member and the distance between the lock member docking section and the lock exit opening (e.g., distal-most end of the catheter) of the lock deployment catheter may be selected to provide a pre-selected amount of slack and/or reduction in implant tension. The pre-selected amount of slack provided may allow for a greater degree of motion of the ventricular walls (e.g., as depicted in FIGS. 16A-16B), which may help facilitate the recovery of ventricular function.

Various lock deployment catheters with a lock member docking section that is offset from the lock exit opening are depicted in FIGS. 20A-20C. They each have an offset distance (dx) between the lock member docking section and the lock exit opening (which is, in these variations is, the distal-most opening of the catheter lumen). A lock deployment catheter (2000) may comprise an elongate body (2002), a longitudinal lumen (2004) terminating at a distal-most opening (2010), a lock member docking section (2001), a lock member (2006) retained at the docking section (2001), and a push member (2008) located within the lumen (2004). The lock member (2006) may comprise a plug (2005) and a tube (2007) configured to receive the plug. The tether of an implant may be threaded through an opening in the wall of the elongate body (2002) through an opening of the lock member tube (2007) such that the plug (2005) can engage the tether when distally advanced by the push member (2008). The lock member docking section (2001) may be located at distance (dx) away from the distal-most opening (2010), and may be, for example, from about 5 mm to about 15 mm, e.g., from about 6 mm to about 11 mm, from about 8 mm to about 10 mm, about 7 mm, about 9.5 mm, etc. FIG. 20B depicts one variation of a lock deployment catheter (2020) with a relatively long offset distance while FIG. 20C depicts one variation of a lock deployment catheter (2040) with a relatively short offset distance. The lock deployment catheter (2020) may provide a greater amount of slack to the implant than the lock deployment catheter (2040).

FIG. 20B depicts one variation of a lock deployment catheter (2020) comprising an elongate body (2022), a longitudinal lumen (2024) terminating at a distal-most opening (2030), a lock member docking section (2021), a lock member 2026 retained at the docking section (2021), and a push member (2028) located within the lumen (2004). The lock member (2026) may comprise a plug (2025) and a tube (2027) configured to receive the plug. The tether of an implant may be threaded through an opening (2032) in the wall of the elongate body (2002) through an opening (2029) of the lock member tube (2027) such that the plug (2025) can engage the tether when distally advanced by the push member (2028). The lock deployment catheter (2020) may also comprise a push member stop member (2034) within the longitudinal lumen to limit distal advancement of the push member. The stop member (2034) may have a lumen through which a portion of the push member may pass. The push member (2028) may comprise stop tube (2023) located along the length of the push member that has a greater diameter than the stop member (2034) such that distal advancement of the push member is blocked when the stop tube contacts the stop member. The stop member (2034) may be a collet, band, ring, etc., that is secured to the internal surface of the lumen (2024). Alternatively, the stop member (2034) may be a region of the lumen with a diameter that is less than the diameter of the stop tube (e.g., a narrowed portion of the lumen). The lock member docking section (2001) may be located at distance or offset (dx) away from the distal-most opening (2010), and may be, for example, from about 5 mm to about 15 mm, e.g., from about 6 mm to about 11 mm, from about 8 mm to about 10 mm, about 7 mm, about 9.5 mm, etc. The lock member may be retained in the docking section by any releasable mechanism, for example, by friction-fit, snap-fit and/or a frangible connection, FIG. 20B depicts another variation of a lock deployment catheter (2040) that is similar to the lock deployment catheter (2020) of FIG. 20B, with a smaller docking section offset (dx), and may be, for example, from about 0.5 mm to about 4 mm. Optionally, the lock deployment catheter may also be configured to tension the tether prior to securing a lock member on the tether.

Methods

Figure 21:
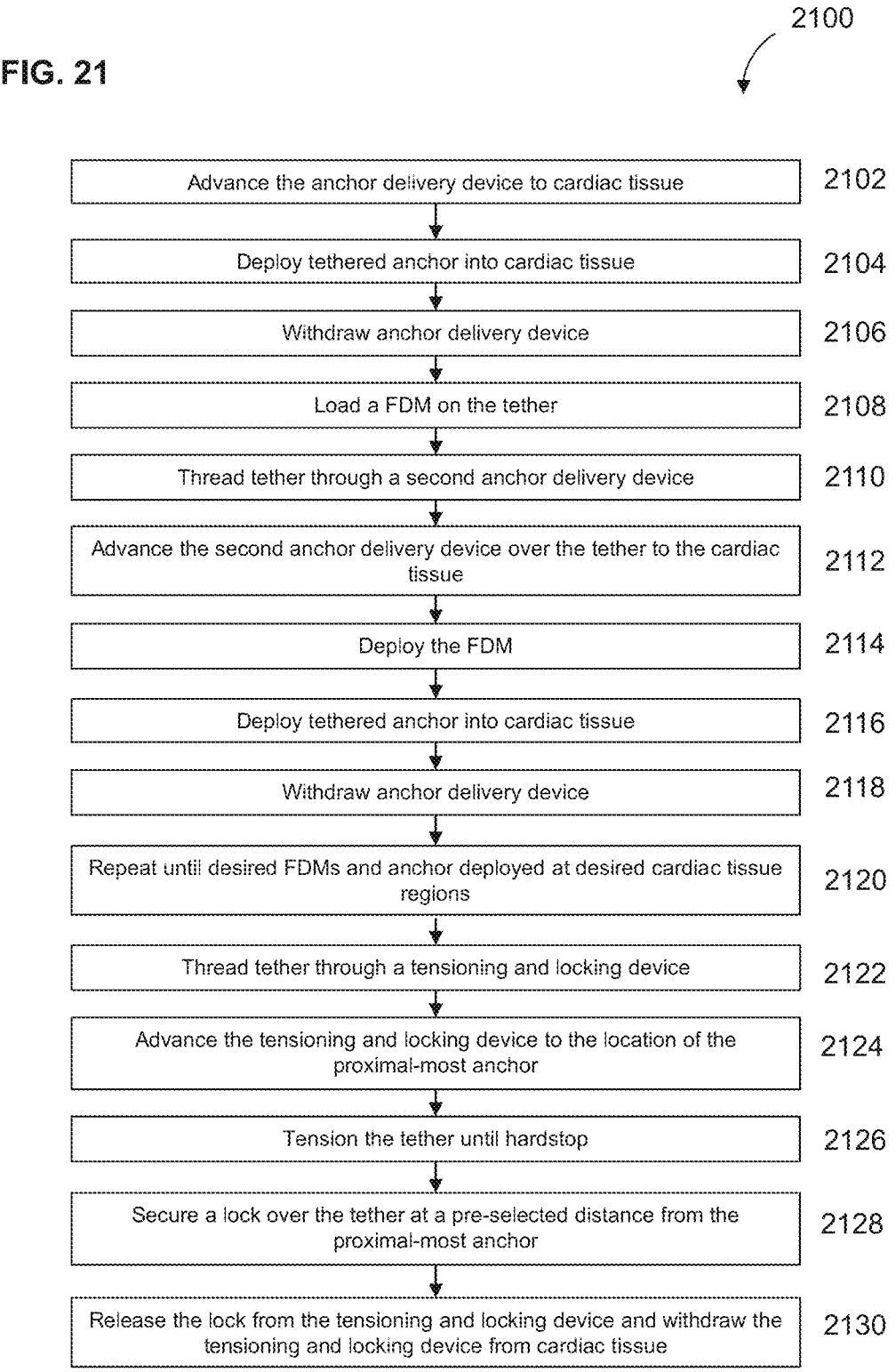
FIG. 21 is a flowchart depiction of one variation of a method for cinching an implant and locking a pre-selected amount of slack on the implant tether.

One variation of a method may comprise delivering an implant comprising a plurality of tethered anchors and one or more FDMs disposed between the tethered anchors to cardiac tissue (e.g., ventricular wall tissue in a subvalvular space), cinching the implant by tensioning the tether until a hard stop (i.e., where further tensioning of the tether does not further cinch the implant) and securing a lock member on the tether with a pre-selected length of tether between the lock member and a proximal end of the implant, wherein the pre-selected length of tether corresponds to a pre-selected amount of slack. The method may further comprise releasing the lock member to provide the pre-selected amount of slack into the implant. One variation of a method may comprise delivering an implant comprising a plurality of tethered anchors and one or more FDMs disposed between the tethered anchors to cardiac tissue (e.g., ventricular wall tissue in a subvalvular space), cinching the implant by tensioning the tether until a peak tether tension, releasing a pre-selected amount of tension from the peak tether tension to an intermediate level of tether tension, and securing a lock member on the tether to maintain the intermediate level of tether tension. In some variations, one or more of the FDMs may be partially or fully bioabsorbable. FIG. 21 depicts a flowchart representation of one variation of a method (2100) for deploying the implants described herein. Method (2100) may comprise advancing (2102) an anchor delivery device to cardiac tissue (e.g., ventricular wall tissue in a subvalvular space), deploying (2104) a tethered anchor into the cardiac tissue, withdrawing (2106) the anchor delivery device, loading (2108) a FDM on the tether, threading the tether (2110) through a second anchor delivery device (through an eyelet of the anchor), advancing (2112) the second anchor delivery device over the tether to the cardiac tissue, deploying (2114) the FDM, deploying (2116) the second tethered anchor into cardiac tissue, and withdrawing (2118) the anchor delivery device. Step (2108) to step (2118) may be repeated (2120) until a desired number of FDMs and tethered anchors have been deployed at the cardiac tissue region. The method (2100) may then comprise threading (2122) the tether through a tensioning and locking device, advancing (2124) the tensioning and locking device to the location of the proximal-most terminal anchor, tensioning (2126) the tether until the implant is in its hard stop configuration (where further tensioning of the tether does not further cinch the implant), securing (2128) a lock member over the tether at a pre-selected distance from the proximal-most terminal anchor, and releasing (2130) the lock member and withdrawing the tensioning and locking device from the cardiac tissue. The tensioning and locking device may be any of the lock deployment catheters of FIGS. 20A-20C, where the lock member is secured with a pre-selected docking section offset (dx) in order to consistently provide a pre-selected amount of slack to the tether. Advancing the tensioning and locking device to the location of the proximal-most anchor may comprise abutting the distal end of the device against the anchor and/or the tissue immediate adjacent to (or in the vicinity of) the proximal-most anchor. The method (2100) may be used to deploy any of the implants disclosed herein to valve tissue (e.g., mitral valve, tricuspid valve), subvalvular tissue including ventricular wall tissue, and the like.

Figure 22A:
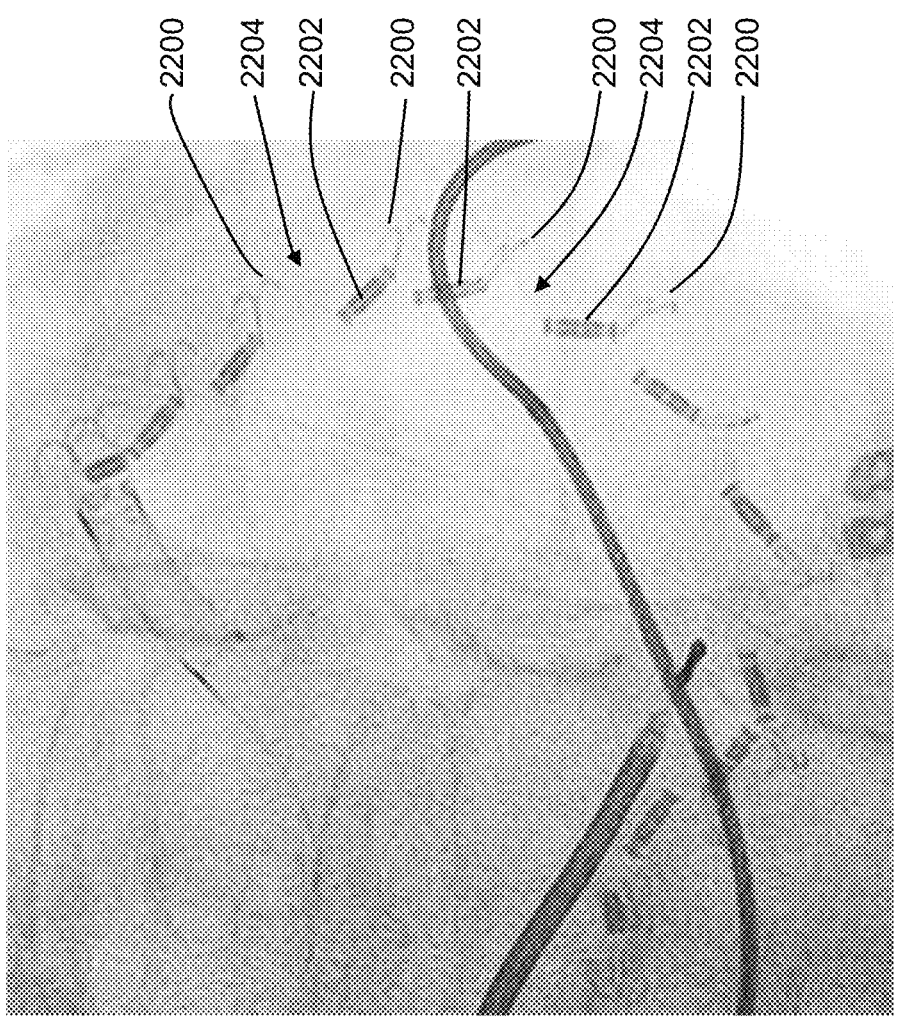
FIGS. 22A-22D are photographic images of a method for cinching an implant and locking a pre-selected amount of slack on the implant tether.
Figure 22B:
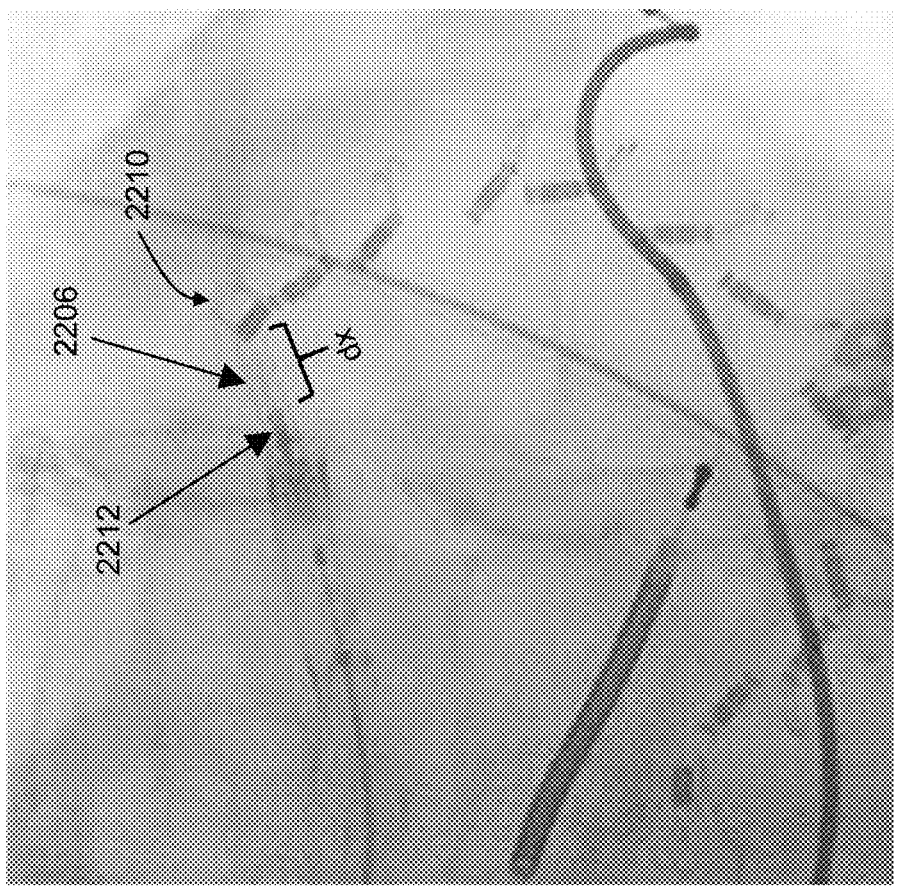
Figure 22C:
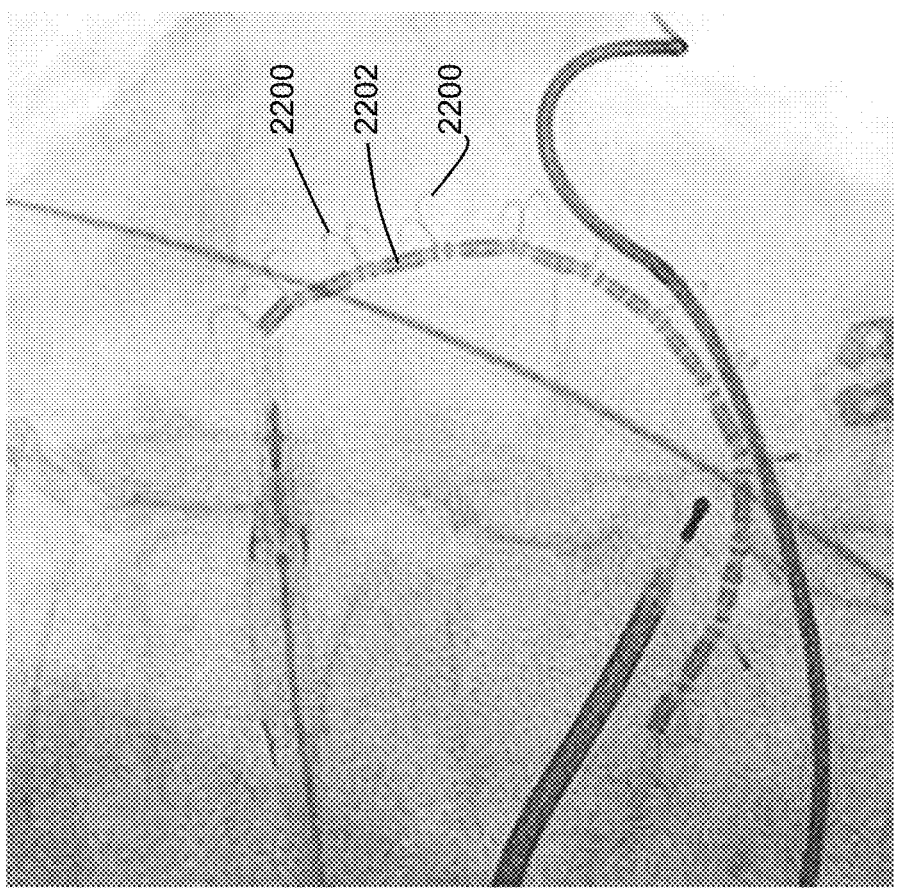
Figure 22D:
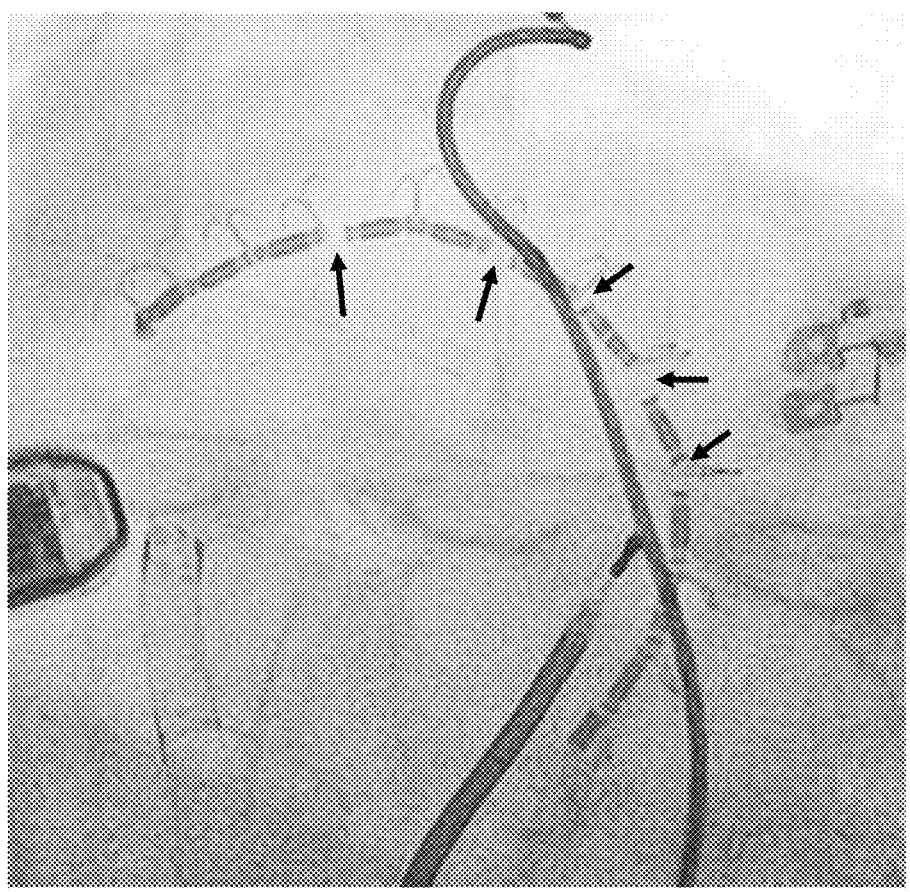

FIGS. 22A-22D depict one example of a procedure that deploys an implant comprising tethered anchors and FDMs to ventricular wall tissue in a subvalvular space (e.g., below the mitral valve). The implant depicted in the photographs for FIGS. 22A-22D may be similar to the implant of FIG. 3A, where the implant comprises a plurality of tethered tissue anchors with FDMs located between each pair of anchors. FIG. 22A depicts the implant after all of the tissue anchors (2200) and FDMs (2202) have been attached to left ventricular wall tissue. The tether has not yet been cinched, and as such, there are gaps (2204) between the anchors and FDMs. FIG. 22B depicts the advancement of the lock deployment catheter (2206) to the ventricular wall, where the distal-most end of the lock deployment catheter (2206) is docked to the implant at the proximal-most terminal anchor (2210). The lock (2212) is located at a distance (dx) away from the distal-most end of the lock deployment catheter. In this example, the docking section offset (dx) is about 7 mm, the lock offset is about 2.5 mm, so the total lock distance offset $d_{offset}$ is about 9.5 mm. FIG. 22C depicts the implant after it has been cinched to its hard stop. As seen there, there are no spaces between the FDMs (2202) and anchors (2200), the anchors are coupled together via the FDMs, and the tether is tensioned throughout the implant. The anchors may be uniform in penetration depth and coupled to each other such that no cinch or tether tension is lose due to subsequent anchor migration (e.g., deeper or more superficially in the tissue). The lock member may be attached to tissue at a total lock distance offset, which may lock in $d_{offset}$ (about 9.5 mm) amount of slack to the tether. As shown in FIG. 22D, the slack may traverse from the proximal-most terminal anchor toward the center region of the implant (e.g., toward the P2 region of the valve), creating gaps between the FDMs and intermediate anchors (see arrows in FIG. 22D). This may help facilitate flexibility during systole, and/or may help promote implant robustness and flexibility. The built-in docking section offset (dx) of the lock deployment catheter may help facilitate precise and consistent introduction of a quantized amount of slack to the implant.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

The invention claimed is:

1. A surgical method for tensioning and locking a tether, the method comprising:
    tensioning a tether of an implant to cinch the implant to its hard stop configuration, where further tensioning of the tether does not further cinch the implant;
    securing a lock member on the tether with a pre-selected length of tether between the lock member and a proximal end of the implant, wherein the pre-selected length of tether corresponds to a pre-selected amount of slack; and
    releasing the lock member to provide the pre-selected amount of slack into the implant.

2. The method of claim 1, wherein the implant comprises a plurality of tethered anchors and force-distribution members located between the anchors in an alternating pattern.

3. The method of claim 2, wherein when the implant is in the hard stop configuration, the tethered anchors and force-distribution members contact each other.

4. The method of claim 3, wherein securing the lock member comprises engaging the lock member on the tether at the pre-selected length away from a proximal-most anchor of the implant.

5. The method of claim 4, wherein the pre-selected length is from about 5 mm to about 15 mm.

6. The method of claim 5, wherein the pre-selected length is about 9.5 mm.

7. The method of claim 2, wherein the pre-selected amount of slack provides a gap from about 2 mm to about 3.5 mm between at least two of the plurality of force-distribution members.

8. The method of claim 7, wherein the pre-selected amount of slack provides a gap of about 2.5 mm between at least two of the plurality of force-distribution members.

9. The method of claim 1, further comprising deploying the implant comprising a plurality of tethered anchors and force-distribution members to ventricular wall tissue in a subvalvular region of a heart.

10. The method of claim 1, wherein the surgical method is a percutaneous procedure.

11. The method of claim 1, further comprising loading the tether in a lock deployment catheter before tensioning the tether, the lock deployment catheter comprising:
    an elongate body having a longitudinal lumen therethrough that terminates at a distal-most opening;
    a lock member docking section located within the lumen that retains the lock member at the pre-selected distance from the distal-most opening; and
    a push member slidably disposed within the longitudinal lumen.

12. The method of claim 11, wherein the pre-selected distance is from about 5 mm to about 15 mm.

13. The method of claim 12, wherein the pre-selected distance is about 9.5 mm.

14. The method of claim 11, wherein the lock member comprises a tube having longitudinal lumen and a side opening, and a plug slidably disposed within the lumen of the tube.

15. The method of claim 14, wherein loading the tether in the lock deployment catheter comprises loading the tether through the side opening of the tube.

16. The method of claim 15, wherein securing the lock member comprises distally sliding the push member to urge the plug into the tube to secure the lock member at the lock member docking section.

17. The method of claim 16, further comprising releasing the lock member from the lock deployment catheter.

* * * * *